United States Patent [19]
Shoji et al.

[11] Patent Number: 5,250,681
[45] Date of Patent: Oct. 5, 1993

[54] PIPERIDINE DERIVATIVES AND HYPOTENSIVES CONTAINING THE SAME

[75] Inventors: Masataka Shoji; Kozo Toyota; Chikahiko Eguchi; Ryota Yoshimoto; Yoshikatsu Koyama; Hideki Domoto; Akira Kamimura, all of Kawasaki, Japan

[73] Assignee: Ajinomoto Co., Inc., Tokyo, Japan

[21] Appl. No.: 655,775

[22] Filed: Feb. 15, 1991

Related U.S. Application Data

[63] Continuation-in-part of Ser. No. 443,438, Nov. 30, 1989, abandoned, which is a continuation-in-part of Ser. No. 354,880, May 22, 1989, which is a continuation-in-part of Ser. No. 201,911, Jun. 2, 1988, abandoned.

[30] Foreign Application Priority Data

Nov. 30, 1988 [JP] Japan ................ 63-303461
Mar. 16, 1989 [JP] Japan ................ 1-64059

[51] Int. Cl.$^5$ .................. C07D 211/70; C07D 487/14
[52] U.S. Cl. ..................... 540/577; 540/586; 546/80; 546/81; 546/89; 546/93; 546/101; 546/195; 546/196; 546/197; 546/198; 546/199; 546/200; 546/201; 546/202; 546/203; 546/204
[58] Field of Search ............ 546/195, 196, 197, 198, 546/199, 200, 201, 202, 203, 204, 80, 81, 89, 93, 101; 514/318, 319, 320, 321, 322, 323, 324, 325; 540/577, 586

[56] References Cited

U.S. PATENT DOCUMENTS

| | | | |
|---|---|---|---|
| 3,014,911 | 12/1961 | Engelhardt | 260/293 |
| 4,031,222 | 6/1977 | Remy | 546/203 X |
| 4,073,912 | 2/1978 | Kaiser | 424/267 |
| 4,356,184 | 10/1987 | Deason | 424/267 |
| 4,891,376 | 1/1990 | Manoury et al. | 546/203 X |
| 4,912,222 | 3/1990 | Griffith et al. | 546/203 |

FOREIGN PATENT DOCUMENTS

| | | |
|---|---|---|
| 730712 | 3/1966 | Canada . |
| 0005607 | 11/1979 | European Pat. Off. . |
| 0347123 | 12/1989 | European Pat. Off. . |
| 1921934 | 11/1969 | Fed. Rep. of Germany . |
| 2256392 | 5/1973 | Fed. Rep. of Germany . |
| 2423721 | 12/1974 | Fed. Rep. of Germany . |
| 2550395 | 5/1976 | Fed. Rep. of Germany . |
| 2290202 | 6/1976 | France . |
| 931555 | 7/1963 | United Kingdom . |
| 1153977 | 6/1969 | United Kingdom . |

OTHER PUBLICATIONS

J. Med. Chem., vol. 17, No. 1, Jan. 1974, pp. 57-62, C. Kaiser et al.: "Analogs of phenothiazines.5. Synthesis and neuropharmacological activity of some piperidylidene derivatives of thioxanthenes, xanthenes, dibenzoxepins, and acridans".

J. Med. Chem., vol. 18, No. 1, Jan. 1975, pp. 1-8, F. J. Villani et al.: "Benzopyranopyridine derivatives.-1.Aminoalkyl derivatives of the azaxanthenes as bronchodilating agents".

Chem. Pharm. Bull., vol. 27, No. 9, 1979, pp. 2056-2060 Y. Nagai et al.: "Studies on psychotropic agents. V. Synthesis of 1-substituted spiro [dibenz [b,f] oxepin-11,-4'-piperidine]-10 (11H)–one and related compounds".

Engelhardt et al, J. Med. Chem., 8(6), 1965, pp. 829-835.

Primary Examiner—Richard L. Raymond
Attorney, Agent, or Firm—Oblon, Spivak, McClelland, Maier & Neustadt

[57] ABSTRACT

A piperidine compound of the formula (I):

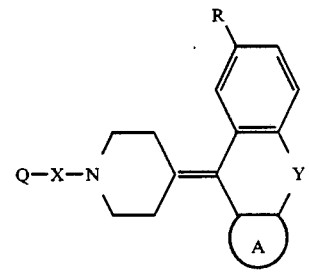

wherein A is a fused aromatic ring; R is hydrogen, chloro or methoxy; X is $(CH_2)_n$, which may be substituted, in which n is 0 or an integer of 1 to 10, —CH=CH—, —C≡C—, —O—, —S—, —NH—, —N(COCH$_3$)—, —N(COOC$_2$H$_5$)—, —N(CHO)—, —N(CH$_3$)—, —CO—, —SO—, or —SO$_2$—; Y is —CH=CH—, —CH$_2$CH$_2$—, —CH$_2$CO—, —O—, —S—, —NH—, —OCH$_2$—, —SCH$_2$—, —NHCH$_2$—, —CH(OH)CH$_2$— or —CH(OH)CH(OH)—; and Q is substituted or unsubstituted n-hexyl, carboxypropyl, ethoxycarbonylpropyl, cyanopropyl, cyclohexyl, phenyl, indanyl, naphthyl, tetrahydronaphthyl, benzocycloheptyl, piperidinyl, tetrahydroisoquinolinyl, indolyl, pyrolyl, furyl, thienyl, thiazolyl, oxazolyl or N-methylpyrolyl, wherein any one or more of the —(CH$_2$)-groups of the hexyl, carboxypropyl, ethoxycarbonylpropyl and cyanopropyl groups may be replaced by —CH=CH—, —C≡C—, —O—, —S—, —NH—, —N(COCH$_3$), —N(COC$_2$H$_5$)—, —N(CHO)—, —N(CH$_3$)—, —CO—, —SO— or —SO$_2$—, and wherein one or more of the —(CH$_2$)-groups in X and Q may be substituted by —(CH$_2$)$_4$— or —(CH$_2$)$_5$— thereby forming a ring structure.

9 Claims, No Drawings

PIPERIDINE DERIVATIVES AND HYPOTENSIVES CONTAINING THE SAME

CROSS REFERENCE TO RELATED APPLICATIONS

This application is a continuation-in-part of application Ser. No. 07/443,438 filed Nov. 30, 1989, now abandoned, which is a continuation-in-part of application Ser. No. 07/354,880 filed May 22, 1989 which is a continuation-in-part of abandoned application Ser. No. 07/201,911 filed Jun. 2, 1988, now abandoned.

BACKGROUND OF THE INVENTION

1. Field of the Invention

The present invention relates to a piperidine derivative and hypotensives containing the same.

2. Description of the Background

It is said that there are about 13,000,000 patients with hypertension in Japan and its frequency of occurrence in individuals becomes greater with advancing age. Further, as the age of a given population increases, increased attention is directed to hypertension which becomes more and more of a dangerous factor in severe heart and cerebral diseases represented by cardiac infarction and cerebral apoplexy. In recent years, calcium antagonists or angiotensin convertase inhibitors have been widely used as excellent primary selection drugs for treatment of hypertension. But the pharmaceutical effects or safety of these hypotensives have recently come into question.

A need therefore continues to exist for new hypotensive agents which exhibit excellent pharmaceutical effects and safety which can be industrially prepared at low cost and in a simple manner.

SUMMARY OF THE INVENTION

Accordingly, one object of the present invention is to provide an effective hypotensive agent which is relatively simple to prepare at low cost.

Briefly, this object and other objects of the present invention as hereinafter will become more readily apparent can be attained by a piperidine derivative of formula (I):

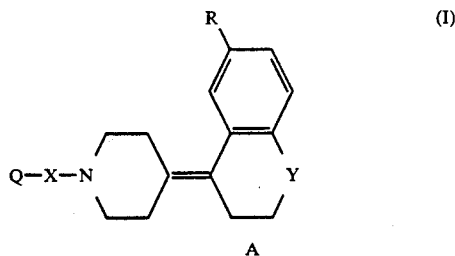

wherein A is a fused aromatic ring; R is hydrogen, chloro or methoxy; X is $(CH_2)_n$, whch may be substituted, in which n is 0 or an integer of 1 to 10, —CH═CH—, —C≡C—, —O—, —S—, —NH—, —N(COCH$_3$)—, —N(COOC$_2$H$_5$)—, —N(CHO)—, —N(CH$_3$)—, —CO—, —SO— or —SO$_2$—; Y is —CH═CH—, —CH$_2$CH$_2$—, —CH$_2$CO—, —O—, —S—, —NH—, —OCH$_2$—, —SCH$_2$—, —NHCH$_2$—, —CH(OH)CH$_2$— or —CH(OH)CH(OH)—; and Q is substituted or unsubstituted n-hexyl, carboxypropyl, ethoxycarbonylpropyl, cyanopropyl, cyclohexyl, phenyl, indanyl, naphthyl, tetrahydronaphthyl, benzocycloheptyl, piperidinyl, tetrahydroisoquinolinyl, indolyl, pyrolyl, furyl, thienyl, thiazolyl, oxazolyl or N-methylpyrolyl, wherein any one or more of the —(CH$_2$)-groups of the hexyl, carboxypropyl, ethoxycarbonylpropyl and cyanopropyl groups may be replaced by —CH═CH—, —C≡C—, —O—, —S—, —NH—, —N(COCH$_3$), —N(COC$_2$H$_5$)—, —N(CHO)—, —N(CH$_3$)—, —CO—, —SO— or —SO$_2$—, and wherein one or more of the —(CH$_2$)-groups in X and Q may be substituted by —(CH$_2$)$_4$— or —(CH$_2$)$_5$— thereby forming a ring structure.

DETAILED DESCRIPTION OF THE PREFERRED EMBODIMENTS

It has now been discovered that piperidine derivatives of the formula (I) above are effective as hypotensive agents. The present piperidine derivative exhibits excellent hypotensive action, its method of synthesis is simple and its derivatives can be easily prepared.

In formula (I), the fused aromatic ring (A) is a fused benzene, thiophene, pyridine or the like ring. Further, in formula (I) above, substituents X and Q may be substituted by at least one substituent selected from the group consisting of H(CH$_2$)$_n$, wherein n is 1 to 10, Cl(CH$_2$)$_3$, allyl phenyl, isopropyl, hydroxy, methoxy, ethoxy, fluoro, chloro, acetoxy, 2-methoxyacetoxy, ethoxycarboxy, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

The method of administration of the present piperidine derivative when used as a hypotensive, include oral and parenteral routes. Dose is determined depending upon age, body weight and condition of the patient and route of administration. Daily dose is generally 0.01 to 2000 mg/kg for oral administration. In the case of parenteral administration, the daily dose is 0.01 to 1000 mg/kg. The present piperidine derivative may be prepared in the form of ordinary preparations such as for example, tablets, powders, capsules, solutions, sugar-coated tablets or depots, which may be prepared in a conventional manner using conventional preparation aids. For example, tablets can be obtained by mixing the piperidine derivative of the present invention diluents (e.g., lactose, calcium carbonate or calcium phosphate), binders (e.g., gum arabic, corn starch or gelatin), swelling agents (e.g., alginic acid, corn starch or pregelinated starch), sweeteners (e.g., sucrose or saccharin), flavors (e.g., peppermint, Gaultheria adenothrix oil or cherry), lubricating and wetting agents (e.g., magnesium stearate, talc or carboxymethyl cellulose).

Having now generally described this invention, a further understanding can be obtained by reference to certain specific examples which are provided herein for purposes of illustration only and are not intended to be limited unless otherwise specified.

Unless otherwise indicated, the developing conditions for silica gel TLC procedures were under chloroform/methanol=9/1. Mass spectra (MS) were performed in the FD mode (m/z) and nuclear magnetic resonance spectra (NMR) were measured using tetramethylsilane as the internal standard and CDCl$_3$ as the solvent.

EXAMPLE 1

4-(5H-Dibenzo[a,d]cyclohepten-5-ylidene)-1-hexylpiperidine hydrochloride

A solution of 273 mg (1 mmol) of 4-(5H-dibenzo[a,d]cyclohepten-5-ylidene)-1-hexylpiperidine, 165 mg (1 mmol) of 1-bromohexane, 745 mg (5 mmols) of sodium iodide and 414 mg (3 mmols) of potassium carbonate in 20 ml of methyl isobutyl ketone was stirred and refluxed at 120° C. overnight on an oil bath. After the reaction, the mixture was washed by adding 20 ml of water thereto. Then the organic phase was separated and the solvent was distilled off under reduced pressure. After purifying by silica gel column chromatography (eluent: methanol/chloroform, 1/100–1/50), the product was converted into the hydrochloride with an equimolar hydrogen chloride/dioxane solution.

Amount yielded 180 mg
Yield 46%
TLC Rf=0.68
MS 357 (M+)
NMR 0.83 (3H, t), 1.2–1.4 (6H, m), 1.7–1.9 (2H, m), 2.31 (2H, dd), 2.53 (2H, d), 2.7–2.8 (2H, m), 3.14 (2H, dd), 3.38 (2H, dd), 3.38 (2H, d), 6.92 (2H, s), 7.2–7.4 (8H, m)

Hereafter procedures were carried out in a manner similar to Example 1.

EXAMPLE 2

4-(5H-Dibenzo[a,d]cyclohepten-5-ylidene)-1-octylpiperidine hydrochloride
Amount yielded 300 mg
Yield 72%
TLC Rf=0.71
MS 385 (M+)
NMR 0.85 (3H, t), 1.2–1.4 (10H, m), 1.7–2.0 (2H, m), 2.30 (2H, dd), 2.53 (2H, d), 2.7–2.9 (2H, m), 3.13 (2H, dd), 3.38 (2H, d), 6.90 (2H, s), 7.1–7.4 (8H, m)

EXAMPLE 3

1-Decyl-4-(5H-dibenzo[a,d]cyclohepten-5-ylidene)-piperidine hydrochloride
Amount yielded 300 mg
Yield 67%
TLC Rf=0.75
MS 413 (M+)
NMR 0.85 (3H, t), 1.2–1.4 (14H, m), 1.7–1.9 (2H, m), 2.33 (2H, dd), 2.54 (2H, d), 2.7–2.8 (2H, m), 3.15 (2H, dd), 3.39 (2H, d), 6.92 (2H, s), 7.1–7.4 (8H, m)

EXAMPLE 4

4-(5H-Dibenzo[a,d]cyclohepten-5-ylidene)-1-dodecylpiperidine hydrochloride
Amount yielded 1.10 g
Yield 92%
TLC Rf=0.78
MS 441 (M+)
NMR 0.85 (3H, t), 1.1–1.5 (18H, m), 1.7–1.9 (2H, m), 2.32 (2H, dd), 2.54 (2H, d), 2.7–2.8 (2H, m), 3.12 (2H, dd), 3.36 (2H, d), 6.93 (2H, s), 7.1–7.4 (8H, m)

EXAMPLE 5

4-(5H-Dibenzo[a,d]cyclohepten-5-ylidene)-1-tetradecylpiperidine hydrochloride
Amount yielded 1.20 g
Yield 95%
TLC Rf=0.78
MS 469 (M+)
NMR 0.82 (3H, t), 1.1–1.5 (22H, m), 1.7–1.9 (2H, m), 2.33 (2H, dd), 2.55 (2H, d), 2.7–2.8 (2H, m), 3.15 (2H, dd), 3.40 (2H, d), 6.92 (2H, s), 7.1–7.4 (8H, m)

EXAMPLE 6

4-(5H-Dibenzo[a,d]cyclohepten-5-ylidene)-1-hexadecylpiperidine hydrochloride
Amount yielded 1.18 g
Yield 88%
TLC Rf=0.80
MS 497 (M+)
NMR 0.80 (3H, t), 1.1–1.6 (26H, m), 1.7–1.9 (2H, m), 2.33 (2H, dd), 2.58 (2H, d), 2.7–2.8 (2H, m), 3.20 (2H, dd), 3.40 (2H, d), 6.88 (2H, s), 7.1–7.4 (8H, m)

EXAMPLE 7

1-Cyclohexylmethyl-4-(5H-dibenzo[a,d]cyclohepten-5-ylidene)piperidine hydrochloride
Amount yielded 520 mg
Yield 51%
TLC Rf=0.75
MS 369 (M+)
NMR 0.8–2.1 (11H, m), 2.42 (2H, dd), 2.65 (2H, d), 2.78 (2H, d), 3.20 (2H, dd), 3.42 (2H, d), 6.91 (2H, s), 7.1–7.4 (8H, m)

EXAMPLE 8

1-Cyclohexyl-2-(4-(5H-dibenzo[a,d]cyclohepten-5-ylidene)-1-piperidinyl)ethane hydrochloride
Amount yielded 780 mg
Yield 74%
TLC Rf=0.75
MS 383 (M+)
NMR 0.8–2.1 (13H, m), 2.45 (2H, dd), 2.67 (2H, d), 2.7–2.9 (2H, m), 3.0 (2H, dd), 3.48 (2H, d), 6.94 (2H, s), 7.1–7.4 (8H, m)

EXAMPLE 9

1-Cyclohexyl-3-(4-(5H-dibenzo[a,d]cyclohepten-5-ylidene)-1-piperidinyl)propane hydrochloride
Amount yielded 1.02 g
Yield 94%
TLC Rf=0.77
MS 397 (M+)
NMR 0.8–2.1 (15H, m), 2.47 (2H, dd), 2.68 (2H, d), 2.7–2.9 (2H, m), 3.0 (2H, dd), 3.49 (2H, d), 6.94 (2H, s), 7.1–7.4 (8H, m)

EXAMPLE 10

1-Cyclohexyl-4-(4-(5H-dibenzo[a,d]cyclohepten-5-ylidene)-1-piperidinyl)butane hydrochloride
Amount yielded 815 mg
Yield 72%
TLC Rf=0.78
MS 411 (M+)
NMR 0.8–2.1 (17H, m), 2.28 (2H, dd), 2.52 (2H, d), 2.7–2.9 (2H, m), 3.08 (2H, dd), 3.35 (2H, d), 6.92 (2H, s), 7.1–7.4 (8H, m)

EXAMPLE 11

1-Cyclohexyl-5-(4-(5H-dibenzo[a,d]cyclohepten-5-ylidene)-1-piperidinyl)pentane hydrochloride
Amount yielded 750 mg
Yield 65%
TLC RF=0.80
MS 411 (M+)

NMR 0.8–2.1 (19H, m), 2.25 (2H, dd), 2.68 (2H, d), 2.7–2.9 (2H, m), 3.12 (2H, dd), 3.38 (2H, d), 6.92 (2H, s), 7.1–7.4 (8H, m)

EXAMPLE 12

1-Benzyl-4-(5H-dibenzo[a,d]cyclohepten-5-ylidene)-piperidien hydrochloride
Amount yielded 320 mg
Yield 80%
TLC Rf=0.42
MS 363 (M+)
NMR 2.28 (2H, dd), 2.52 (2H, d), 3.14 (2H, dd), 3.31 (2H, d), 4.01 (2H, d), 6.90 (2H, s), 7.1–7.6 (13H, m)

EXAMPLE 13

2-(4-(5H-Dibenzo[a,d]cyclohepten-5-ylidene)-1-piperidinyl)-1-phenylethane hydrochloride
Amount yielded 310 mg
Yield 75%
TLC Rf=0.45
MS 377 (M+)
NMR 2.28 (2H, dd), 2.51 (2H, d), 3.0–3.3 (6H, m), 3.47 (2H, d), 6.90 (2H, s), 7.1–7.4 (13H, m)

EXAMPLE 14

3-(4-(5H-Dibenzo[a,d]cyclohepten-5-ylidene)-1-piperidinyl)-1-phenylpropane hydrochloride
Amount yielded 330 mg
Yield 77%
TLC Rf=0.50
MS 391 (M+)
NMR 2.1–2.4 (4H, m), 2.51 (2H, d), 2.65 (2H, t), 2.7–2.9 (2H, m), 3.12 (2H, dd), 3.38 (2H, d), 6.90 (2H, s), 7.1–7.4 (13H, m)

EXAMPLE 15

4-(4-(5H-Dibenzo[a,d]cyclohepten-5-ylidene)-1-piperidinyl)-1-phenylbutane hydrochloride
Amount yielded 180 mg
Yield 41%
TLC Rf=0.50
MS 405 (M+)
NMR 1.4–1.9 (4H, m), 2.28 (2H, dd), 2.52 (2H, d), 2.61 (2H,t), 2.7–2.8 (2H, m), 3.12 (2H, dd), 3.35 (2H, d), 6.90 (2H, s), 7.1–7.4 (13H, m)

EXAMPLE 16

5-(4-(5H-Dibenzo[a,d]cyclohepten-5-ylidene)-1-piperidinyl)-1-phenylpentane hydrochloride
Amount yielded 110 mg
Yield 24%
TLC Rf=0.55
MS 419 (M+)
NMR 1.2–1.9 (6H, m), 2.25 (2H, dd), 2.52 (2H, d), 2.60 (2H, t), 2.7–2.8 (2H, m), 3.08 (2H, dd), 3.35 (2H, d), 6.90 (2H, s), 7.1–7.4 (13H, m)

EXAMPLE 17

6-(4-(5H-Dibenzo[a,d]cyclohepten-5-ylidene)-1-piperidinyl)-1-phenylhexane hydrochloride
Amount yielded 315 mg
Yield 67%
TLC Rf=0.56
MS 433 (M+)
NMR 1.1–1.9 (8H, m), 2.26 (2H, dd), 2.56 (2H, d), 2.61 (2H, t), 2.7–2.8 (2H, m), 3.10 (2H, dd), 3.35 (2H, d), 6.91 (2H, s), 7.1–7.4 (13H, m)

EXAMPLE 18

7-(4-(5H-Dibenzo[a,d]cyclohepten-5-ylidene)-1-piperidinyl)-1-phenylheptane hydrochloride
Amount yielded 267 mg
Yield 55%
TLC Rf=0.56
MS 447 (M+)
NMR 1.1–1.9 (10H, m), 2.25 (2H, dd), 2.55 (2H, d), 2.65 (2H, t), 2.7–2.8 (2H, m), 3.07 (2H, dd), 3.32 (2H, d), 6.90 (2H, s), 7.1–7.4 (13H, m)

EXAMPLE 19

2-(4-(5H-Oibenzo[a,d]cyclohepten-5-ylidene)-1-piperidinyl)-1-phenoxyethane hydrochloride
Amount yielded 1.95 g
Yield 55%
TLC Rf=0.56
MS 393 (M+)
NMR (fee base) 2.1–2.5 (2H, m), 2.58 (2H, t), 2.6–2.7 (2H, m), 4.05 (2H, t), 6.89 (2H, d), 6.92 (2H, s), 7.1–7.4 (11H, m)

EXAMPLE 20

3-(4-(5H-Dibenzo[a,d]cyclohepten-5-ylidene)-1-piperidinyl)-1-phenoxypropane hydrochloride
Amount yielded 2.15 g
Yield 48%
TLC Rf=0.58
MS 407 (M+)
NMR (free base) 1.97 (2H, tt), 2.1–2.5 (6H, m), 2.54 (2H, t), 2.6–2.7 (2H, m), 3.97 (2H, dd), 6.86 (2H, d), 6.90 (2H, s), 7.1–7.4 (11H, m)

EXAMPLE 21

4-(4-(5H-Dibenzo[a,d]cyclohepten-5-ylidene)-1-piperidinyl)-1-phenoxybutane hydrochloride
Amount yielded 1.18 g
Yield 86%
TLC Rf=0.61
MS 421 (M+)
NMR (free base) 1.8–2.7 (14H, m), 3.96 (2H, t), 6.87 (2H, d), 6.90 (2H, s), 7.1–7.4 (11H, m)

EXAMPLE 22

2-(4-(5H-dibenzo[a,d]cyclohepten-5-ylidene)-1-piperidinyl)-1-phenylthioethane hydrochloride
Amount yielded 0.97 g
Yield 87%
TLC Rf=0.55
MS 409 (M+)
NMR (free base) 2.0–2.6 (10H, m), 2.78 (2H, t), 6.86 (2H, s), 7.1–7.4 (11H, m)

EXAMPLE 23

3-(4-(5H-Dibenzo[a,d]cyclohepten-5-ylidene)-1-piperidinyl)-1-phenylthiopropane hydrochloride
Amount yielded 0.85 g
Yield 74%
TLC Rf=0.62
MS 423 (M+)
NMR (free base) 1.73 (2H, tt), 2.0–2.6 (10H, m), 2.80 (2H, t), 6.88 (2H, d), 7.1–7.4 (11H, m)

EXAMPLE 24

4-(4-(5H-Dibenzo[a,d]cyclohepten-5-ylidene)-1-piperidinyl)-1-phenylthiobutane hydrochloride
Amount yielded 0.85 g Yield 72%
TLC Rf=0.62
MS 437 (M+)
NMR (free base) 1.6-2.6 (14H, m), 2.80 (2H, t), 6.88 (2H, d), 7.1-7.4 (11H, m)

EXAMPLE 25

4-(5H-Dibenzo[a,d]cyclohepten-5-ylidene)-1-(2-(2-nitrobenzenesulfonyl)aminoethyl)piperidine hydrochloride
TLC Rf=0.72
MS 502 (M+)

EXAMPLE 26

1-(2-(2-Aminobenzenesulfonyl)aminoethyl)-4-(5H-dibenzo[a,d]-cyclohepten-5-ylidene)piperidine hydrochloride
TLC Rf=0.51
MS 472 (M+)

EXAMPLE 27

4-(5H-Dibenzo[a,d]cyclohepten-5-ylidene)-1-(2-(2-ethoxycarbon-ylbenzenesulfon6yl)aminoethyl)piperidine hydrochloride
TLC Rf=0.68
MS 544 (M+)

EXAMPLE 28

3-(2-((4-(5H-Dibenzo[a,d]cyclohepten-5-ylidene)-1-piperidinyl)-ethyl)-2,4(1H,3H)quinazolinedione hydrochloride
TLC Rf=0.85
MS 462 (M+)

EXAMPLE 29

5,6-Benzo-2,4-diazo(2-(4-(5H-dibenzo[a,d]cyclohepten-5-ylidene)-1-piperidinyl)ethyl)tetrahydrothiopyrane hydrochloride
TLC Rf=0.91
MS 498 (M+)

EXAMPLE 30

2-(4-(5H-Dibenzo[a,d]cyclohepten-5-ylidene)-1-piperidinyl)-1-(3,4-dimethoxyphenyl)ethane hydrochloride
TLC Rf=0.78
MS 450 (M+)

EXAMPLE 31

5-(4-(5H-Dibenzo[a,d]cyclohepten-5-ylidene)-1-piperidinyl)-2-(3,4-dimethoxyphenyl)-2-isopropyl-valeronitrile hydrochloride
TLC Rf=0.92
MS 532 (M+)
NMR 0.77 (3H, d), 1.18 (3H, d), 1.6-3.3 (15H, m), 3.86 (3H, s), 3.92 (3H, s), 6.8-7.4 (11H, m)

EXAMPLE 32

3-(4-(5H-Dibenzo[a,d]cyclohepten-5-ylidene)-1-piperidinyl)-propyl-4-fluorophenylsulfoxide hydrochloride
TLC Rf=0.78
MS 457 (M+)

EXAMPLE 33

3-(4-(5H-Dibenzo[a,d]cyclohepten-5-ylidene)-1-piperidinyl)-propyl-4-fluorophenylsulfone hydrochloride
TLC Rf=0.62
MS 473 (M+)

EXAMPLE 34

4-(5H-Dibenzo[a,d]cyclohepten-5-ylidene)-1-(3-(2-aminophenylthio)-1-propyl)piperidine hydrochloride
TLC Rf=0.84
MS 439 (M+)

EXAMPLE 25

4-(5H-Dibenzo[a,d]cyclohepten-5-ylidene)-1-(1-(2-benzoylamino)ethyl)piperidine hydrochloride
TLC Rf=0.84
MS 420 (M+)

EXAMPLE 36

4-(5H-Dibenzo[a,d]cyclohepten-5-ylidene)-1-(1-(2-N-phenylcarbamoylamino)ethyl)piperidine hydrochloride
TLC Rf=0.55
MS 435 (M+)

EXAMPLE 37

1-(3-(2-Cinnamoylaminophenylthio)-1-propyl)-4-(5H-dibenzo[a,d]-cyclohepten-5-ylidene)piperidine hydrochloride
TLC Rf=0.66
MS 568 (M+)
NMR (free base) 1.74 (2H, tt), 2.0-2.6 (8H, m), 2.80 (2H, t), 6.59 (1H, d), 6.88 (2H, s), 7.0-7.6 (16H, m), 7.75 (1H, d), 8.5 (1H, d), 8.68 (1H, bs)

EXAMPLE 38

1-Cinnamyl-4-(5H-dibenzo[a,d]cyclohepten-5-ylidene)-piperidine hydrochloride
TLC Rf=0.84
MS 389 (M+)
NMR (free base) 2.1-2.7 (8H, m), 3.15 (2H, d), 6.25 (1H, td), 6.47 (1H, d), 6.90 (2H, s), 7.1-7.4 (13H, m)

EXAMPLE 39

5-(4-(5H-Dibenzo[a,d]cyclohepten-5-ylidene)-1-piperidinyl)-2-(3,4,5-trimethoxyphenyl)-2-isopropyl-valeronitrile hydrochloride
TLC Rf=0.80
MS 563 (M+)

EXAMPLE 40

2-(3-(4-(5H-Dibenzo[a,d]cyclohepten-5-ylidene)-1-piperidinyl)-1-propyl)-2-phenyl-1,3-dithiane-1,1,3,3-tetroxide hydrochloride
TLC Rf=0.48
MS 573 (M+)

EXAMPLE 41

2-(3,4-Dimethoxyphenyl)-2-(3-(4-(5H-dibenzo[a,d]cyclohepten-5-ylidene)-1-piperidinyl)-1-propyl)-1,3-dithiane-1,1,3,3-tetroxide hydrochloride
TLC Rf=0.48
MS 573 (M+)

EXAMPLE 42

5-(4-(5H-Dibenzo[a,d]cyclohepten-5-ylidene)-1-piperidinyl)-2-(3,4-dichlorophenyl)-2-isopropyl-valeronitrile hydrochloride
TLC Rf=0.94
MS 540 (M+)

EXAMPLE 43

2-(3-Benzoylphenyl)-5-(4-(5H-dibenzo[a,d]cyclohepten-5-ylidene)-1-piperidinyl)-2-methylvaleronitrile hydrochloride
TLC Rf=0.88
MS 548 (M+)

EXAMPLE 44

5-(4-(5H-Dibenzo[a,d]cyclohepten-5-ylidene)-1-piperidinyl)-2,2-diphenylvaleronitrile hydrochloride
TLC Rf=0.74
MS 506 (M+)

EXAMPLE 45

4-(4-(5H-Dibenzo[a,d]cyclohepten-5-ylidene)-1-piperidinyl)-3,4-dimethoxybutyrophenone hydrochloride
TLC Rf=0.61
MS 479 (M+)

EXAMPLE 46

6-(4-(5H-Dibenzo[a,d]cyclohepten-5-ylidene)-1-piperidinyl)-2phenylhexanenitrile hydrochloride
TLC Rf=0.86
MS 430 (M+)

EXAMPLE 47

6-(4-(5H-Dibenzo[a,d]cyclohepten-5-ylidene)-1-piperidinyl)-2-isopropyl-2-phenylhexanenitrile hydrochloride
TLC Rf=0.88
MS 472 (M+)

EXAMPLE 48

6-(4-(5H-Dibenzo[a,d]cyclohepten-5-ylidene)-1-piperidinyl)-2-(3,4-dimethoxyphenyl)-2-isopropylhexanenitrile hydrochloride
TLC Rf=0.81
MS 546 (M+)

EXAMPLE 49

7-(4-(5H-Dibenzo[a,d]cyclohepten-5-ylidene)-1-piperidinyl)-2-phenylheptanenitrile hydrochloride
TLC Rf=0.84
MS 444 (M+)

EXAMPLE 50

7-(4-(5H-Dibenzo[a,d]cyclohepten-5-ylidene)-1-piperidinyl)-2-isopropyl-2-phenylheptanenitrile hydrochloride
TLC Rf=0.84
MS 486 (M+)

EXAMPLE 51

7-(4-(5H-Dibenzo[a,d]cyclohepten-5-ylidene)-1-piperidinyl)-2-(3,4-dimethoxyphenyl)-2-isopropylheptanenitrile hydrochloride
TLC Rf=0.86
MS 560 (M+)

EXAMPLE 52

2-(3-Chloropropyl)-5-(4-(5H-dibenzo[a,d]cyclohepten-5-ylidene)-1-piperidinyl)-2-phenylvaleronitrile hydrochloride
TLC Rf=0.92
MS 506 (M+)

EXAMPLE 53

5-(4-(5H-Dibenzo[a,d]cyclohepten-5-ylidene)-1-piperidinyl)-2-phenyl-2-phenylthiovaleronitrile hydrochloride
TLC Rf=0.81
MS 538 (M+)

EXAMPLE 54

5-(4-(5H-Dibenzo[a,d]cyclohepten-5-ylidene)-1-piperidinyl)-2-(3,4-dimethoxyphenyl)-2-phenylthiovaleronitrile hydrochloride
TLC Rf=0.91
MS 598 (M+)

EXAMPLE 55

5-(4-(5H-Dibenzo[a,d]cyclohepten-5-ylidene)-1-piperidinyl)-2-(1-naphthyl)valeronitrile hydrochloride
TLC Rf=0.85
MS 580 (M+)

EXAMPLE 56

5-(4-(5H-Dibenzo[a,d]cyclohepten-5-ylidene)-1-piperidinyl)-2-(1-naphthyl)-2-isopropylvaleronitrile hydrochloride
TLC Rf=0.90
MS 522 (M+)

EXAMPLE 57

5-(4-(5H-Dibenzo[a,d]cyclohepten-5-ylidene)-1-piperidinyl)-2-(2-naphthyl)valeronitrile hydrochloride
TLC Rf=0.85
MS 480 (M+)

EXAMPLE 58

5-(4-(5H-Dibenzo[a,d]cyclohepten-5-ylidene)-1-piperidinyl)-2-(2-naphthyl)-2-isopropylvaleronitrile hydrochloride
TLC Rf=0.87
MS 522 (M+)

EXAMPLE 59

5-(4-(5H-Dibenzo[a,d]cyclohepten-5-ylidene)-1-piperidinyl)-2-(3-trifluoromethylphenyl)valeronitrile hydrochloride
TLC Rf=0.72
MS 498 (M+)

EXAMPLE 60

5-(4-(5H-Dibenzo[a,d]cyclohepten-5-ylidene)-1-piperidinyl)-2-isopropyl-2-(3-trifluoromethylphenyl)valeronitrile hydrochloride
TLC Rf=0.75
MS 540 (M+)

EXAMPLE 61

8-(4-(5H-Dibenzo[a,d]cyclohepten-5-ylidene)-1-piperidinyl)-2-phenyloctanenitrile hydrochloride
TLC Rf=0.84
MS 472 (M+)

EXAMPLE 62

8-(4-(5H-Dibenzo[a,d]cyclohepten-5-ylidene)-1-piperidinyl)-2-isopropyl-2-phenyloctanenitrile hydrochloride
TLC Rf=0.88

MS 514 (M+)

EXAMPLE 63

8-(4-(5H-Dibenzo[a,d]cyclohepten-5-ylidene)-1-piperidinyl)-2-(3,4-dimethoxyphenyl)-2-isopropyloctanenitrile hydrochloride
TLC Rf=0.82
MS 574 (M+)

EXAMPLE 64

1-(3-(4-(5H-Dibenzo[a,d]cyclohepten-5-ylidene)-1-piperidinyl)-1-propyl)-1-indanenitrile hydrochloride
TLC Rf=0.90
MS 456 (M+)

EXAMPLE 65

1-(3-(4-(5H-Dibenzo[a,d]cyclohepten-5-ylidene)-1-piperidinyl)-1-propyl)-5,6-dimethoxy-1-indanenitrile hydrochloride
TLC Rf=0.85
MS 516 (M+)

EXAMPLE 66

5-(4-(5H-Dibenzo[a,d]cyclohepten-5-ylidene)-1-piperidinyl)-2-(1-methylpyrrol-2-yl)valeronitrile hydrochloride
TLC Rf=0.61
MS 433 (M+)

EXAMPLE 67

5-(4-(5H-Dibenzo[a,d]cyclohepten-5-ylidene)-1-piperidinyl)-2-isopropyl-2-(1-methylpyrrol-2-yl)valeronitrile hydrochloride
TLC Rf=0.71
MS 475 (M+)

EXAMPLE 68

5-(4-(5H-Dibenzo[a,d]cyclohepten-5-ylidene)-1-piperidinyl)-2-isopropyl-2-(pyrrol-2-yl)valeronitrile hydrochloride
TLC Rf=0.55
MS 461 (M+)

EXAMPLE 69

5-(4-(5H-Dibenzo[a,d]cyclohepten-5-ylidene)-1-piperidinyl)-2-(3-α-hydroxybenzyl)phenyl)-2-methylvaleronitrile hydrochloride
TLC Rf=0.51
MS 550 (M+)

EXAMPLE 70

2-(3-Benzoylphenyl)-6-(4-(5H-Dibenzo[a,d]cyclohepten-5-ylidene)-1-piperidinyl)-2-methylhexanenitrile hydrochloride
TLC Rf=0.88
MS 562 (M+)

EXAMPLE 71

6-(4-(5H-Dibenzo[a,d]cyclohepten-5-ylidene)-1-piperidinyl)-2-(3-(α-hydroxybenzyl)phenyl-2-methylhexanenitrile hydrochloride
TLC Rf=0.52
MS 564 (M+)

EXAMPLE 72

2-(3-Benzoylphenyl)-7-(4-(5H-Dibenzo[a,d]cyclohepten-5-ylidene)-1-piperidinyl)-2-methylheptanenitrile hydrochloride
TLC Rf=0.91
MS 576 (M+)

EXAMPLE 73

7-(4-(5H-Dibenzo[a,d]cyclohepten-5-ylidene)-1-piperidinyl)-2-(3-(α-hydroxybenzyl)phenyl-2-methylheptanenitrile hydrochloride
TLC Rf=0.52
MS 578 (M+)

EXAMPLE 74

2-(3-Benzoylphenyl)-8-(4-(5H-Dibenzo[a,d]cyclohepten-5-ylidene)-1-piperidinyl)-2-methyloctanenitrile hydrochloride
TLC Rf=0.90
MS 590 (M+)

EXAMPLE 75

8-(4-(5H-Dibenzo[a,d]cyclohepten-5-ylidene)-1-piperidinyl)-2-(3-(α-hydroxybenzyl)phenyl-2-methyloctanenitrile hydrochloride
TLC Rf=0.61
MS 592 (M+)

EXAMPLE 76

5-(4-(5H-Dibenzo[a,d]cyclohepten-5-ylidene)-1-piperidinyl)-2-methyl-2-phenylvaleronitrile hydrochloride
TLC Rf=0.91
MS 544 (M+)

EXAMPLE 77

5-(4-(5H-Dibenzo[a,d]cyclohepten-5-ylidene)-1-piperidinyl)-2-(3,4-dimethoxyphenyl)-2-methylvaleronitrile hydrochloride
TLC Rf=0.85
MS 504 (M+)

EXAMPLE 78

5-(4-(5H-Dibenzo[a,d]cyclohepten-5-ylidene)-1-piperidinyl)-2-ethyl-2-phenylvaleronitrile hydrochloride
TLC Rf=0.92
MS 458 (M+)

EXAMPLE 79

5-(4-(5H-Dibenzo[a,d]cyclohepten-5-ylidene)-1-piperidinyl)-2-(3,4-dimethoxyphenyl)-2-ethylvaleronitrile hydrochloride
TLC Rf=0.90
MS 518 (M+)

EXAMPLE 80

5-(4-(5H-Dibenzo[a,d]cyclohepten-5-ylidene)-1-piperidinyl)-2-propyl-2-phenylvaleronitrile hydrochloride
TLC Rf=0.93
MS 472 (M+)

EXAMPLE 81

5-(4-(5H-Dibenzo[a,d]cyclohepten-5-ylidene)-1-piperidinyl)-2-(3,4-dimethoxyphenyl)-2-propylvaleronitrile hydrochloride
TLC Rf=0.91
MS 532 (M+)

EXAMPLE 82

2-Butyl-5-(4-(5H-Dibenzo[a,d]cyclohepten-5-ylidene)-1-piperidinyl)-2-phenylvaleronitrile hydrochloride
TLC Rf=0.95
MS 486 (M+)

EXAMPLE 83

2-Butyl-5-(4-(5H-Dibenzo[a,d]cyclohepten-5-ylidene)-1-piperidinyl)-2-(3,4-dimethoxyphenyl)valeronitrile hydrochloride:
TLC Rf=0.90
MS 546 (M+)

EXAMPLE 84

5-(4-(5H-Dibenzo[a,d]cyclohepten-5-ylidene)-1-piperidinyl)-2-pentyl-2-phenylvaleronitrile hydrochloride:
TLC Rf=0.95
MS 500 (M+)

EXAMPLE 85

5-(4-(5H-Dibenzo[a,d]cyclohepten-5-ylidene)-1-piperidinyl)-2-(3,4-dimethoxyphenyl)-2-pentyl-valeronitrile hydrochloride:
TLC Rf=0.92
MS 560 (M+)

EXAMPLE 86

5-(4-(5H-Dibenzo[a,d]cyclohepten-5-ylidene)-1-piperidinyl)-2-hexyl-2-=henylvaleronitrile hydrochloride:
TLC Rf=0.95
MS 514 (M+)

EXAMPLE 87

5-(4-(5H-Dibenzo[a,d]cyclohepten-5-ylidene)-1-piperidinyl)-2-(3,4-dimethoxyphenyl)-2-hexyl-valeronitrile hydrochloride:
TLC Rf=0.92
MS 574 (M+)

EXAMPLE 88

5-(4-(5H-Dibenzo[a,d]cyclohepten-5-ylidene)-1-piperidinyl)2-heptyl-2-phenylvaleronitrile hydrochloride:
TLC Rf=0.95
MS 528 (M+)

EXAMPLE 89

5-(4-(5H-Dibenzo[a,d]cyclohepten-5-ylidene)-1-piperidinyl)-2-(3,4-dimethoxyphenyl)-2-heptyl-valeronitrile hydrochloride:
TLC Rf=0.91
MS 588 (M+)

EXAMPLE 90

5-(4-(5H-Dibenzo[a,d]cyclohepten-5-ylidene)-1-piperidinyl)-2-octyl-2-phenylvaleronitrile hydrochloride:
TLC Rf=0.94
MS 542 (M+)

EXAMPLE 91

5-(4-(5H-Dibenzo[a,d]cyclohepten-5-ylidene)-1-piperidinyl)-2-octylvaleronitrile hydrochloride:
TLC Rf=0.94
MS 602 (M+)

EXAMPLE 92

5-(4-(5H-Dibenzo[a,d]cyclohepten-5-ylidene)-1-piperidinyl)-2-nonyl-2-phenylvaleronitrile hydrochloride:
TLC Rf=0.95
MS 556 (M+)

EXAMPLE 93

5-(4-(5H-Dibenzo[a,d]cyclohepten-5-ylidene)-1-piperidinyl)-2-(3,4-dimethoxyphenyl)-2-nonyl-valeronitrile hydrochloride:
TLC Rf=0.93
MS 616 (M+)

EXAMPLE 94

2-Decyl-5-(4-(5H-Dibenzo[a,d]cyclohepten-5-ylidene)-1-piperidinyl)-2-phenylvaleronitrile hydrochloride:
TLC Rf=0.95
MS 570 (M+)

EXAMPLE 95

2-Decyl-5-(4-(5H-Dibenzo[a,d]cyclohepten-5-ylidene)-1-piperidinyl)-2-(3,4-dimethoxyphenyl)valeronitrile hydrochloride:
TLC Rf=0.94
MS 630 (M+)

EXAMPLE 96

5-(4-(5H-Dibenzo[a,d]cyclohepten-5-ylidene)-1-piperidinyl)-acetophenone hydrochloride:
TLC Rf=0.71
MS 391 (M+)

EXAMPLE 97

2-(4-(5H-Dibenzo[a,d]cyclohepten-5-ylidene)-1-piperidinyl)-1-hydroxy-1-phenylethane hydrochloride:
TLC Rf=0.36
MS 393 (M+)

EXAMPLE 98

3-(4-(5H-Dibenzo[a,d]cyclohepten-5-ylidene)-1-piperidinyl)-propiophenone hydrochloride:
TLC Rf=0.74
MS 405 (M+)

EXAMPLE 99

3-(4-(5H-Dibenzo[a,d]cyclohepten-5-ylidene)-1-piperidinyl)1-hydroxy-1-phenylpropane hydrochloride:
TLC Rf=0.35
MS 407 (M+)

EXAMPLE 100

3-(4-(5H-Dibenzo[a,d]cyclohepten-5-ylidene)-1-piperidinyl)-butyrophenone hydrochloride:
TLC Rf=0.75
MS 419 (M+)

EXAMPLE 101

4-(4-(5H-Dibenzo[a,d]cyclohepten-5-ylidene)-1-piperidinyl)-1-hydroxy-1-phenylbutane hydrochloride:
TLC Rf=0.39
MS 421 (M+)

EXAMPLE 102

5-(4-(5H-Dibenzo[a,d]cyclohepten-5-ylidene)-1-piperidinyl)-valerophenone hydrochloride:
TLC Rf=0.76
MS 433 (M+)

EXAMPLE 103

5-(5H-Dibenzo[a,d]cyclohepten-5-ylidene)-1-piperidinyl)-1-hydroxy-1-phenylpentane hydrochloride:
TLC Rf=0.78
MS 447 (M+)

EXAMPLE 104

2-(4-(5H-Dibenzo[a,d]cyclohepten-5-ylidene)-1-piperidinyl)-4'-fluoroacetophenone hydrochloride:
TLC Rf=0.80
MS 409 (M+)

EXAMPLE 105

2-(4-(5H-Dibenzo[a,d]cyclohepten-5-ylidene)-1-piperidinyl)1-hydroxy-1-(4-fluorophenyl)ethane hydrochloride:
TLC Rf=0.44
MS 411 (M+)

EXAMPLE 106

3-(4-(5H-Dibenzo[a,d]cyclohepten-5-ylidene)-1-piperidinyl)4'-fluoropropiophenone hydrochloride:
TLC Rf=0.80
MS 423 (M+)

EXAMPLE 107

3-(4-(5H-Dibenzo[a,d]cyclohepten-5-ylidene)-1-piperidinyl)-1-hydroxy-1-(4-fluorophenyl)propane hydrochloride:
TLC Rf=0.44
MS 425 (M+)

EXAMPLE 108

4-(4-(5H-Dibenzo[a,d]cyclohepten-5-ylidene)-1-piperidinyl)-1-hydroxy-1-(4-fluorophenyl)butane hydrochloride:
TLC Rf=0.45
MS 439 (M+)

EXAMPLE 109

5-(4-(5H-Dibenzo[a,d]cyclohepten-5-ylidene)-1-piperidinyl)-4'-fluorovalerophenone hydrochloride:
TLC Rf=0.84
MS 451 (M+)

EXAMPLE 110

5-(4-(5H-Dibenzo[a,d]cyclohepten-5-ylidene)-1-piperidinyl)-1-hydroxy-1-(4-fluorophenyl)pentane hydrochloride:
TLC Rf=0.51
MS 453 (M+)

EXAMPLE 111

4-(5H-Dibenzo[a,d]cyclohepten-5-ylidene)-1-(2-fluorobenzyl)-piperidine hydrochloride:
TLC Rf=0.75
MS 381(M+)

EXAMPLE 112

4-(5H-Dibenzo[a,d]cyclohepten-5-ylidene)-1-(3-fluorobenzyl)piperidine hydrochloride:
TLC Rf=0.79
MS 381 (M+)

EXAMPLE 113

4-(5H-Dibenzo[a,d]cyclohepten-5-ylidene)-1-(4-fluorobenzyl)piperidine hydrochloride:
TLC Rf=0.61
MS 381 (M+)

EXAMPLE 114

4-(5H-Dibenzo[a,d]cyclohepten-5-ylidene)-1-(2-trifluoromethylbenzyl)piperidine hydrochloride:
TLC Rf=0.83
MS 431 (M+)

EXAMPLE 115

4-(5H-Dibenzo[a,d]cyclohepten-5-ylidene)-1-(3-trifluoromethylbenzyl)piperidine hydrochloride:
TLC Rf=0.82
MS 431 (M+)

EXAMPLE 116

5-(4-(5H-Dibenzo[a,d]cyclohepten-5-ylidene)-1-piperidine hydrochloride:
TLC Rf=0.79
MS 431 (M+)

EXAMPLE 117

4-(5H-Dibenzo[a,d]cyclohepten-5-ylidene)-1-(2-methoxybenzyl)piperidine hydrochloride:
TLC Rf=0.61
MS 393 (M+)

EXAMPLE 118

4-(5H-Dibenzo[a,d]cyclohepten-5-ylidene)-1-(3-methoxybenzyl)piperidine hydrochloride:
TLC Rf=0.61
MS 393 (M+)

EXAMPLE 119

4-(5H-Dibenzo[a,d]cyclohepten-5-ylidene)-1-(4-methoxybenzyl)piperidine hydrochloride:
TLC Rf=0.52
MS 393 (M+)

EXAMPLE 120

4-(5H-Dibenzo[a,d]cyclohepten-5-ylidene)-1-pentafluorobenzylpiperidine hydrochloride:
TLC Rf=0.80
MS 453 (M+)

EXAMPLE 121

5-(4-(5H-Dibenzo[a,d]cyclohepten-5-ylidene)-1-piperidinyl)-2-phenylvaleronitrile hydrochloride:
TLC Rf=0.86
MS 440 (M+)

EXAMPLE 122

5-(4-(5H-Dibenzo[a,d]cyclohepten-5-ylidene)-1-piperidinyl)-2-isopropyl-2-phenylvaleronitrile hydrochloride:
TLC Rf=0.82
MS 488 (M+)

EXAMPLE 123

5-(4-(5H-Dibenzo[a,d]cyclohepten-5-ylidene)-1-piperidinyl)-2-(3,4-dimethoxyphenyl)valeronitrile hydrochloride:
TLC Rf=0.75
MS 500 (M+)

EXAMPLE 124

2-(3-(4-(5H-Dibenzo[a,d]cyclohepten-5-ylidene)-1-piperidinyl)-1-propyl-2-(4-fluorophenyl)-1,3-dioxolane hydrochloride:
TLC Rf=0.68
MS 481 (M+)

EXAMPLE 125

4-(4-(5H-Dibenzo[a,d]cyclohepten-5-ylidene)-1-piperidinyl)-4'-fluorobutyrophenone hydrochloride:
TLC Rf=0.82
MS 437 (M+)

EXAMPLE 126

5-(4-(5H-Dibenzo[a,d]cyclohepten-5-ylidene)-1-piperidinyl)-2 isopropyl-2-(3,4,5trimethoxyphenyl)-valeronitrile hydrochloride:
TLC Rf=0.66
MS 562 (M+)

| exp | compound | MS(M+) | TLC (Rf) | solvent |
|---|---|---|---|---|
| 127 | 2-(4-(5H-Dibenzo[a,d]cyclohepten-5-ylidene)-1-piperidinyl)-1-(4-fluorophenyl)ethane hydrochloride | 395 | 0.55 | B |
| 128 | 1-(2-Chlorobenzyl)-4-(5H-dibenzo[a,d]cyclohepten-5-ylidene)piperidine hydrochloride | 397 | 0.68 | B |
| 129 | 1-(3-Chlorobenzyl)-4-(5H-dibenzo[a,d]cyclohepten-5-ylidene)piperidine hydrochloride | 397 | 0.58 | B |
| 130 | 1-(4-Chlorobenzyl)-4-(5H-dibenzo[a,d]cyclohepten-5-ylidene)piperidine hydrochloride | 397 | 0.58 | B |
| 131 | 4-(5H-Dibenzo[a,d]cyclohepten-5-ylidene)-1-(2-methylbenzyl)piperidine hydrochloride | 377 | 0.74 | B |
| 132 | 4-(5H-Dibenzo[a,d]cyclohepten-5-ylidene)-1-(3-methylbenzyl)piperidine hydrochloride | 377 | 0.71 | B |
| 133 | 4-(5H-Dibenzo[a,d]cyclohepten-5-ylidene)-1-(4-methylbenzyl)piperidine hydrochloride | 377 | 0.65 | B |
| 134 | 4-(5H-Dibenzo[a,d]cyclohepten-5-ylidene)-1-heptylpiperidine hydrochloride | 371 | 0.70 | B |
| 135 | 4-(5H-Dibenzo[a,d]cyclohepten-5-ylidene)-1-nonylpiperidine hydrochloride | 399 | 0.75 | B |
| 136 | 4-(5H-Dibenzo[a,d]cyclohepten-5-ylidene)-1-undecylpiperidine hydrochloride | 427 | 0.75 | B |
| 137 | 4-(5H-Dibenzo[a,d]cyclohepten-5-ylidene)-1-tridecylpiperidine hydrochloride | 455 | 0.78 | B |
| 138 | 1-(2-Aminobenzyl)-4-(5H-dibenzo[a,d]cyclohepten-5-ylidene)piperidine dihydrochloride | 392 | 0.38 | B |
| 139 | 1-(3-Aminobenzyl)-4-(5H-dibenzo[a,d]cyclohepten-5-ylidene)piperidine dihydrochloride | 392 | 0.23 | B |
| 140 | 1-(4-Aminobenzyl)-4-(5H-dibenzo[a,d]cyclohepten-5-ylidene)piperidine dihydrochloride | 392 | 0.26 | B |
| 141 | 4-(5H-Dibenzo[a,d]cyclohepten-5-ylidene)-1-(2-nitrobenzyl)piperidine hydrochloride | 422 | 0.85 | B |
| 142 | 4-(5H-Dibenzo[a,d]cyclohepten-5-ylidene)-1-(3-nitrobenzyl)piperidine hydrochloride | 422 | 0.82 | B |
| 143 | 4-(5H-Dibenzo[a,d]cyclohepten-5-ylidene)-1-(4-nitrobenzyl)piperidine hydrochloride | 422 | 0.83 | B |
| 144 | 5-(4-(5H-Dibenzo[a,d]cyclohepten-5-ylidene)-1-piperidinyl)-2-(3-fluorophenyl)-2-isopropylvaleronitrile hydrochloride | 500 | 0.71 | B |
| 145 | 5-(4-(5H-Dibenzo[a,d]cyclohepten-5-ylidene)-1-piperidinyl)-2-isopropyl-2-(3-methoxyhenyl)valeronitrile hydrochloride | 512 | 0.64 | B |
| 146 | 5-(4-(5H-Dibenzo[a,d]cyclohepten-5-ylidene)-1-piperidinyl)-2-isopropyl-2-(3-methylphenyl)valeronitrile hydrochloride | 496 | 0.68 | B |
| 147 | 5-(4-(5H-Dibenzo[a,d]cyclohepten-5-ylidene)-1-piperidinyl)-2-isopropyl-2-(2-trifluoromethylphenyl)valeronitrile hydrochloride | 549 | 0.78 | B |
| 148 | 5-(4-(5H-Dibenzo[a,d]cyclohepten-5-ylidene)-1-piperidinyl)-2-isopropyl-2-(4-trifluoromethylphenyl)valeronitrile hydrochloride | 540 | 0.77 | B |
| 149 | 5-(4-(5H-Dibenzo[a,d]cyclohepten-5-ylidene)-1-piperidinyl)-2-ethyl-2-(3-trifluoromethylphenyl)valeronitrile hydrochloride | 526 | 0.77 | B |
| 150 | 2-Butyl-5-(4-(5H-dibenzo[a,d]cyclohepten-5-ylidene)-1-piperidinyl)-2-(3-trifluoromethylphenyl)valeronitrile hydrochloride | 554 | 0.80 | B |
| 151 | 5-(4-(5H-Dibenzo[a,d]cyclohepten-5-ylidene)-1-piperidinyl)-2-hexyl-2-(3-trifluoromethylphenyl)valeronitrile hydrochloride | 582 | 0.80 | B |
| 152 | 4-(4-(5H-Dibenzo[a,d]cyclohepten-5-ylidene)-1-piperidinyl)-1-phenyl-1-butene hydrochloride | 403 | 0.51 | B |
| 153 | 1-Benzyloxy-2-(4-(5H-Dibenzo[a,d]cyclohepten-5-ylidene)-1-piperidinyl)ethane hydrochloride | 407 | 0.58 | B |
| 154 | 1-Cylcohexyl-6-(4-(5H-dibenzo[a,d]cyclohepten-5-ylidene)-1-piperidinyl)hexane hydorchloride | 439 | 0.62 | B |
| 155 | 1-Cylcohexyl-7-(4-(5H-dibenzo[a,d]cyclohepten-5-ylidene)-1-piperidinyl)heptane hydorchloride | 453 | 0.65 | B |
| 156 | 1-Cylcohexyl-8-(4-(5H-dibenzo[a,d]cyclohepten-5-ylidene)-1-piperidinyl)octane hydorchloride | 467 | 0.68 | B |
| 157 | 1-(4-Cyclohexylbutanoyl)-4-(5H-dibenzo[a,d]cyclohepten-5-ylidene)piperidine | 425 | 0.75 | B |
| 158 | 1-(2-Cyanobenzyl)-4-(5H-dibenzo[a,d]cyclohepten-5-ylidene)piperidine hydrochloride | 388 | 0.83 | B |
| 159 | 1-(3-Cyanobenzyl)-4-(5H-dibenzo[a,d]cyclohepten-5-ylidene)piperidine hydrochloride | 388 | 0.85 | B |
| 160 | 1-(4-Cyanobenzyl)-4-(5H-dibenzo[a,d]cyclohepten-5-ylidene)piperidine hydrochloride | 388 | 0.70 | B |
| 161 | 4-(5H-Dibenzo[a,d]cyclohepten-5-ylidene)-1-(2-Picolyl)piperidine dihydrochloride | 364 | 0.58 | B |
| 162 | 4-(5H-Dibenzo[a,d]cyclohepten-5-ylidene)-1-(3-Picolyl)piperidine dihydrochloride | 364 | 0.53 | B |
| 163 | 4-(5H-Dibenzo[a,d]cyclohepten-5-ylidene)-1-(4-Picolyl)piperidine dihydrochloride | 364 | 0.44 | B |
| 164 | 1-Decanoyl-4-(5H-dibenzo[a,d]cyclohepten-5-ylidene)piperidine | 427 | 0.75 | B |
| 165 | 1-Cyano-3-(4-(5H-dibenzo[a,d]cyclohepten-5-ylidene)-1-piperidinyl)propane hydrochloride | 340 | 0.58 | B |
| 166 | 1-Cyano-4-(4-(5H-dibenzo[a,d]cyclohepten-5-ylidene)-1-piperidinyl)butane hydrochloride | 354 | 0.52 | B |
| 167 | 2-(4-(5H-Dibenzo[a,d]cyclohepten-5-ylidene)-1-piperidinyl)-3',4'-dimetoxyacetophenone hydrochloride | 451 | 0.85 | B |
| 168 | 3-(4-(5H-Dibenzo[a,d]cyclohepten-5-ylidene)-1-piperidinyl)-3',4'-dimetoxypropiophenone hydrochloride | 465 | 0.61 | B |
| 169 | 5-(4-(5H-Dibenzo[a,d]cyclohepten-5-ylidene)-1-piperidinyl)-3',4'-dimetoxyvalerophenone hydrochloride | 493 | 0.64 | B |
| 170 | 4-(4-(5H-Dibenzo[a,d]cyclohepten-5-ylidene)-1-piperidinyl)-3',4',5'-trimetoxybutyrophenone hydrochloride | 509 | 0.82 | B |
| 171 | 4-(4-(5H-Dibenzo[a,d]cyclohepten-5-ylidene)-1-piperidinyl)-2',3',4'-trimetoxybutyrophenone hydrochloride | 509 | 0.85 | B |
| 172 | 4-(4-(5H-Dibenzo[a,d]cyclohepten-5-ylidene)-1-piperidinyl)-4'-metoxybutyrophenone hydrochloride | 449 | 0.61 | B |
| 173 | 4-(5H-Dibenzo[a,d]cyclohepten-5-ylidene)-1-(2,3-dimethoxybenzyl)piperidine hydrochloride | 423 | 0.63 | B |
| 174 | 4-(5H-Dibenzo[a,d]cyclohepten-5-ylidene)-1-(3,4-dimethoxybenzyl)piperidine hydrochloride | 423 | 0.73 | B |
| 175 | 4-(5H-Dibenzo[a,d]cyclohepten-5-ylidene)-1-(3,4-dimethoxybenzoyl)piperidine | 437 | 0.58 | B |
| 176 | 1-Cyclohexyl-3-(4-(5H-dibenzo[a,d]cyclohepten-5-ylidene)-1-piperidinyl)propylketone hydrochloride | 425 | 0.51 | B |

-continued

| exp | compound | MS(M+) | TLC (Rf) | solvent |
|---|---|---|---|---|
| 177 | 2-Cyclohexyl-5-(4-(5H-dibenzo[a,d]cyclohepten-5-ylidene)-1-piperidinyl)valeronitrile hydrochloride | 436 | 0.60 | B |
| 178 | 1-(4-(3-Chloro-5H-dibenzo[a,d]cyclohepten-5-ylidene)-1-piperidinyl)-4-cyclohexylbutane hydrochloride | 445 | 0.62 | B |
| 179 | 1-Cyclohexyl-(4-(3-metoxy-5H-dibenzo[a,d]cyclohepten-5-ylidene)-1-piperidinyl)butane hydrochloride | 441 | 0.59 | B |
| 180 | 4,9-Dihydro-4-(1-(4-cyclohexylbutyl)-4-piperidinylidene)-10H-benzo[4,5]cyclohepta[1,2-b]biophen-10-one hydrochloride | 433 | 0.45 | B |
| 181 | 1-(4-Cyclohexylbutyl)-4-(9-xantylidene)piperidine hydrochloride | 401 | 0.64 | B |
| 182 | 1-(4-Cyclohexylbutyl)-4-(9-tioxantylidene)piperidine hydrochloride | 417 | 0.65 | B |
| 183 | 6,11-Dihydro-11-(1-(4-cyclohexylbutyl)-4-piperidinylidene)-5H-benzo[5,6]cyclohepta[1,2-b]pyridine dihydrochloride | 414 | 0.41 | B |
| 184 | 4-(10,11-Dihydro-5H-dibenzo[a,d]cyclohepten-5-ylidene)-1-(3-metoxybenzyl)piperidine hydrochloride | 395 | 0.73 | B |
| 185 | 1-Decyl-4-(10,11-Dihydro-5H-dibenzo[a,d]cyclohepten-5-ylidene)piperidine hydrochloride | 415 | 0.52 | H |
| 186 | 1-Cyclohexyl-4-(4-(10,11-Dihydro-5H-dibenzo[a,d]cyclohepten-5-ylidene)-1-piperidinyl)butane hydrochloride | 413 | 0.67 | H |
| 187 | 4-(4-(10,11-Dihydro-5H-dibenzo[a,d]cyclohepten-5-ylidene)-1-piperidinyl)-3',4'-dimetoxybutyrophenone hydrochloride | 481 | 0.66 | B |
| 188 | 4-(5H-Dibenzo[a,d]cyclohepten-5-ylidene)-1-(3,4,5-trimetoxybenzyl)piperidine | 453 | 0.69 | B |
| 189 | 4-(5H-Dibenzo[a,d]cyclohepten-5-ylidene)-1-(3,4,5-trimetoxybenzoyl)piperidine | 467 | 0.71 | B |
| 190 | 4-(5H-Dibenzo[a,d]cyclohepten-5-ylidene)-1-(2-methylbenzoyl)piperidine | 391 | 0.73 | B |
| 191 | 4-(5H-Dibenzo[a,d]cyclohepten-5-ylidene)-1-(2-(4-fluorophenyl)acetyl)piperidine | 409 | 0.76 | B |
| 192 | 4-(5H-Dibenzo[a,d]cyclohepten-5-ylidene)-1-(3,4-dimetoxycinnamoyl)piperidine | 463 | 0.73 | B |
| 193 | 4-(5H-Dibenzo[a,d]cyclohepten-5-ylidend)-1-(3,4-dimetoxycinnamyl)piperidine hydrochloride | 449 | 0.46 | B |
| 194 | 4-(4-(5H-dibenzo[a,d]cyclohepten-5-ylidene)-1-piperidinyl)-3',4'-diethoxybutyrophenone hydrochloride | 501 | 0.49 | B |
| 195 | 1-(4-(4-Aminophenyl)butyl)-4-(5H-dibenzo[a,d]cyclohepten-5-ylidene)piperidine dihydrochloride | 420 | 0.34 | B |
| 196 | 4-(5H-Dibenzo[a,d]cyclohepten-5-ylidene)-1-(4-(4-nitrophenyl)butyl)piperidine hydrochloride | 450 | 0.50 | B |
| 197 | 1-(4-(4-Acetylaminophenyl)butyl)-4-(5H-dibenzo[a,d]cyclohepten-5-ylidene)piperidine dihydrochloride | 462 | 0.48 | B |
| 198 | 4-(4-(5H-Dibenzo[a,d]cyclohepten-5-ylidene)-1-piperidinyl)-3',4'-dimethylbutyrophenone hydrochloride | 447 | 0.53 | B |
| 199 | Ethyl 4-(4-(5H-dibenzo[a,d]cyclohepten-5-ylidene)-1-piperidinyl)butyrate hydrochloride | 387 | 0.51 | B |
| 200 | 4-(4-(5H-Dibenzo[a,d]cyclohepten-5-ylidene)-1-piperidinyl)butyric acid | 359 | 0.15 | B |
| 201 | 4-(5H-Dibenzo[a,d]cyclohepten-5-ylidene)-1-(3-(3',4'-dimethoxyphenyl)propyl)piperidine hydrochloride | 451 | 0.60 | B |
| 202 | 4-(5H-Dibenzo[a,d]cyclohepten-5-ylidene)-1-(3-(3',4'-dimethoxyphenyl)propanoyl)piperidine | 465 | 0.78 | B |
| 203 | 1-(4-(4-(5H-Dibenzo[a,d]cyclohepten-5-ylidene)-1-piperidinyl)butanoyl)piperidine hydrochloride | 426 | 0.60 | B |
| 204 | N-(4-(4-(5H-Dibenzo[a,d]cyclohepten-5-ylidene)-1-piperidinyl)butanoyl)-1,2,3,4-tetrahydroisoquinoline hydrochloride | 474 | 0.42 | B |
| 205 | 4-(4-(5H-Dibenzo[a,d]cyclohepten-5-ylidene)-1-piperidinyl)-1-(3,4-dimethoxy)phenyl-1-hydroxybutane hydrochloride | 481 | 0.38 | B |
| 206 | 1-Acetoxy-4-(4-(5H-dibenzo[a,d]cyclohepten-5-ylidene)-1-piperidinyl)-1-(3,4-dimethoxy)phenylbutane hydrochloride | 523 | 0.49 | B |
| 207 | 1-Butyl-4-(4-(5H-dibenzo[a,d]cyclohepten-5-ylidene)-1-piperidinyl)-1-(3,4-dimethoxy)phenyl-1-hydroxybutane hydrochloride | 537 | 0.45 | B |
| 208 | 1-(4-Metoxycyclohexyl)-4-(4-(5H-dibenzo[a,d]cyclohepten-5-ylidene)-1-piperidinyl)butane hydrochloride | 441 | 0.55 | B |
| 209 | 1-(4-(4-(5H-Dibenzo[a,d]cyclohepten-5-ylidene)-1-piperidinyl)butyl)piperidine dihydrochloride | 412 | 0.03 | B |
| 210 | 4-(5H-Dibenzo[a,d]cyclohepten-5-ylidene)-1-(4-(N-imidazolylmethyl)cinnamyl)piperidine dihydrochloride | 469 | 0.44 | B |
| 211 | 4-(5H-Dibenzo[a,d]cyclohepten-5-ylidene)-1-(2-naphtoyl)piperidine | 427 | 0.88 | B |
| 212 | 4-(5H-Dibenzo[a,d]cyclohepten-5-ylidene)-1-(2-naphtylmethyl)piperidine hydrochloride | 413 | 0.94 | B |
| 213 | 4-(5H-Dibenzo[a,d]cyclohepten-5-ylidene)-1-(1-naphtoyl)piperidine | 427 | 0.59 | B |
| 214 | 4-(5H-Dibenzo[a,d]cyclohepten-5-ylidene)-1-(1-naphtylmethyl)piperidine hydrochloride | 413 | 0.83 | B |
| 215 | 2-(4-(4-(5H-Dibenzo[a,d]cyclohepten-5-ylidene)-1-piperidinyl)butyl)cyclohexanone hydrochloride | 426(H+) | 0.50 | B |
| 216 | 1-(4-(4-(5H-Dibenzo[a,d]cyclohepten-5-ylidene)-1-piperidinyl)butanoyl)-4-hydroxypiperidine hydrochloride | 442 | 0.58 | B |
| 217 | 1-(4-(4-(5H-Dibenzo[a,d]cyclohepten-5-ylidene)-1-piperidinyl)butanoyl)-4-ethoxycarbonylpiperazine hydrochloride | 499 | 0.26 | B |
| 218 | Cyclohexyl 3-(4-(5H-Dibenzo[a,d]cyclohepten-5-ylidene)-1-piperidinyl)propylether hydrochloride | 413 | 0.48 | B |
| 219 | 1-(4-(4-(5H-Dibenzo[a,d]cyclohepten-5-ylidene)-1-piperidinyl)-1-butyl)-1-methoxycarbonylcyclohexane hydrochloride | 470(H+) | 0.55 | B |
| 220 | Ethyl 2-cyclohexyl-5-(4-(5H-dibenzo[a,d]cyclohepten-5-ylidene)-1-piperidinyl)valerate hydrochloride | 483 | 0.65 | B |
| 221 | 3-(5H-Dibenzo[a,d]cyclohepten-5-ylidene)-1-(4-(3',4'-dimethoxyphenyl)butyl)piperidine hydrochloride | 465 | 0.66 | B |
| 222 | 2-(3-(4-(5H-Dibenzo[a,d]cyclohepten-5-ylidene)-1-piperidinyl)-1-propyl-2-(3,4-dimethoxyphenyl)-1,3-dioxolane hydrochloride | 523 | 0.54 | B |
| 223 | 1-Carboxyl-1-(4-(4-(5H-Dibenzo[a,d]cyclohepten-5-ylidene)-1-piperidinyl)butylcyclohexane hydrochloride | 456(H+) | 0.38 | B |
| 224 | 4-(5H-Dibenzo[a,d]cyclohepten-5-ylidene)-1-(1,2,3,4-tetrahydro-2-naphtoyl)piperidine | 431 | 0.90 | B |
| 225 | 4-(5H-Dibenzo[a,d]cyclohepten-5-ylidene)-1-(1,2,3,4-tetrahydro-2-naphtylmethyl)piperidine | 417 | 0.55 | B |
| 226 | N-(3-(4-(5H-Dibenzo[a,d]cyclohepten-5-ylidene)-1-piperidinyl)propanoyl)cyclohexylamine hydrochloride | 426 | 0.64 | B |
| 227 | 2-(4-(5H-Dibenzo[a,d]cyclohepten-5-ylidene)-1-piperidinyl)ethyl cyclohexanecarboxylate hydrochloride | 427 | 0.71 | B |
| 228 | 4-(4-(5H-Dibenzo[b,e]thiepin-5-ylidene)-1-piperidinyl)-1-cyclohexylbutane hydrochloride | 431 | 0.74 | B |
| 229 | 4-(4-(5H-Dibenzo[b,e]thiepin-5-ylidene)-1-piperidinyl)-3'-4'-dimethoxybutyrophenone hydrochloride | 499 | 0.46 | B |
| 230 | 4-(5H-Dibenzo[a,d]cyclohepten-5-ylidene)-1-(2-nitrocinnamyl)piperidine hydrochloride | 434 | 0.70 | B |
| 231 | 1-(4-Aminocinnamyl)-4-(5H-dibenzo[a,d]cyclohepten-5-ylidene)piperidine dihydrochloride | 404 | 0.36 | B |
| 232 | 1-(4-Acetylaminocinnamyl)-4-(5H-dibenzo[a,d]cyclohepten-5-ylidene)piperidine dihydrochloride | 446 | 0.27 | B |
| 233 | 4-(4-(5H-Dibenzo[a,d]cyclohepten-5-ylidene)-1-piperidinyl)-1-(2-furyl)-1-butanone hydrochloride | 409 | | B |
| 234 | 4-(4-(5H-Dibenzo[a,d]cyclohepten-5-ylidene)-1-piperidinyl)-1-(2-thienyl)-1-butanone hydrochloride | 425 | | B |
| 235 | 3-(4-(5H-Dibenzo[a,d]cyclohepten-5-ylidene)-1-piperidinyl)-1-propyl (2-tetrahydropyranyl) ether hydrochloride | 415 | 0.55 | B |

-continued

| exp | compound | MS(M+) | TLC (Rf) | solvent |
|---|---|---|---|---|
| 236 | Cyclohexyl 3-(4-(5H-Dibenzo[a,d]cycloheptea-5-ylidene)-1-piperidinyl)propionate hydrochloride | 427 | 0.71 | B |
| 237 | N-(2-(5H-Dibenzo[a,d]cyclohepten-5-ylidene)-1-piperidiayl)ethyl-4-nitrobenzamide hydrochloride | 465 | 0.49 | H |
| 238 | 2-Cyclohexyl-4-(4-(5H-dibenzo[a,d]cyclohepten-5-ylidene)-1-piperidinyl)butyric acid | 455 | 0.26 | B |
| 239 | 3-(4-(5H-Dibenzo[a,d]cyclohepten-5-ylidene)-1-piperidinyl)-1-propyl phenylsulphoxide hydrochloride | 409 | 0.29 | H |
| 240 | 2-(2-(4-(5H-Dibenzo[a,d]cyclohepten-5-ylidene)-1-piperidinyl)-1-ethyl)-5',6'-dimethoxyindan hydrochloride | 477 | 0.41 | B |
| 241 | 3-(4-(5H-Dibenzo[a,d]cyclohepten-5-ylidene)-1-piperidinyl)-1-propyl phenylsulphone hydrochloride | 441 | 0.36 | B |
| 242 | N-(2-(5H-Dibenzo[a,d]cyclohepten-5-ylidene)-1-piperidinyl)ethyl-3',4'-dimethoxybenzamide hydrochloride | 480 | 0.44 | G |
| 243 | N-(2-(5H-Dibenzo[a,d]cyclohepten-5-ylidene)-1-piperidinyl)ethyl cyclohexanecarboxamide hydrochloride | 426 | 0.75 | B |
| 244 | N-(2-(5H-Dibenzo[a,d]cyclohepten-5-ylidene)-1-piperidinyl)ethyl isonicotinamide dihydrochloride | 421 | 0.20 | B |
| 245 | 1-(4-(4-(5H-Dibenzo[a,d]cyclohepten-5-ylidene)-1-piperidinyl)butanoyl)morphine hydrochloride | 428 | 0.31 | C |
| 246 | 1-(4-(4-(5H-Dibenzo[a,d]cyclohepten-5-ylidene)-1-piperidinyl)butanoyl)thiomorphorine hydrochloride | 444 | 0.43 | C |
| 247 | 3-(4-(5H-Dibenzo[a,d]cyclohepten-5-ylidene)-1-piperidinyl)-1-(4-nitrophenyl)propane hydrochloride | 436 | 0.34 | H |
| 248 | 1-(4-Aminophenyl)-3-(4-(5H-Dibenzo[a,d]cyclohepten-5-ylidene)-1-piperidinyl)propane dihydrochloride | 406 | 0.33 | B |
| 249 | 1-(4-Acetylaminophenyl)-3-(4-(5H-Dibenzo[a,d]cyclohepten-5-ylidene)-1-piperidinyl)propane dihydrochloride | 448 | 0.43 | B |
| 250 | 3-(4-(5H-Dibenzo[a,d]cyclohepten-5-ylidene)-1-piperidinyl)-1-(2-nitrophenyl)propane hydrochloride | 436 | 0.53 | H |
| 251 | 1-(2-Aminophenyl)-3-(4-(5H-Dibenzo[a,d]cyclohepten-5-ylidene)-1-piperidinyl)propane dihydrochloride | 406 | 0.52 | B |
| 252 | 1-(2-Acetylaminophenyl)-3-(4-(5H-Dibenzo[a,d]cyclohepten-5-ylidene)-1-piperidinyl)propane hydrochloride | 448 | 0.51 | B |
| 253 | 2-(4-(5H-Dibenzo[a,d]cyclohepten-5-ylidene)-1-piperidinyl)-1-ethyl phenylsulphoxide hydrochloride | 425 | 0.20 | H |
| 254 | 2-(4-(5H-Dibenzo[a,d]cyclohepten-5-ylidene)-1-piperidinyl)-1-ethyl phenylsulphone hydrochloride | 455 | 0.71 | B |
| 255 | 2-(4-(5H-Dibenzo[a,d]cyclohepten-5-ylidene)-1-piperidinyl)-1-(2-nitrophenyl)butane hydrochloride | 450 | 0.49 | H |
| 256 | Cyclohexyl-3-(4-(5H-Dibenzo[a,d]cyclohepten-5-ylidene)-1-piperidinyl)-1-propylsulphide hydrochloride | 430(H+) | 0.17 | J |
| 257 | Cyclohexyl-3-(4-(5H-Dibenzo[a,d]cyclohepten-5-ylidene)-1-piperidinyl)-1-propylsulphoxide hydrochloride | 445 | 0.51 | B |
| 258 | Cyclohexyl-3-(4-(5H-Dibenzo[a,d]cyclohepten-5-ylidene)-1-piperidinyl)-1-propylsulphone hydrochloride | 462(H+) | 0.28 | H |
| 259 | Ethyl 2-cyclohexylmethyl-4-(4-(5H-dibenzo[a,d]cyclohepten-5-ylidene)-1-piperidinyl)butyrate hydrochloride | 483 | 0.70 | B |
| 260 | 1-(4-Acetylamino-1-cyclohexyl)-4-(4-(5H-dibenzo[a,d]cyclohepten-5-ylidene)-1-piperidinyl)butane hydrochloride | 468 | 0.43 | B |
| 261 | 2-(2-(4-(5H-Dibenzo[a,d]cyclohepten-5-ylidene)-1-piperidinyl)-1-ethyl)-5',6'-dimethoxy-1-indanone hydrochloride | 477 | 0.41 | B |
| 262 | Ethyl 2-(2-cyclohexylethyl)-3-(4-(5H-dibenzo[a,d]cyclohepten-5-ylidene)-1-piperidinyl)propionate hydrochloride | 483 | 0.74 | B |
| 263 | Cyclohexylmethyl-2-(4-(5H-Dibenzo[a,d]cyclohepten-5-ylidene)-1-piperidinyl)-1-ethylsulfone hydrochloride | 461 | 0.94 | B |
| 264 | Cyclohexylmethyl-2-(4-(5H-Dibenzo[a,d]cyclohepten-5-ylidene)-1-piperidinyl)-1-ethylsulfoxide hydrochloride | 441(H+) | 0.48 | B |
| 265 | Cyclohexylmethyl-2-(4-(5H-Dibenzo[a,d]cyclohepten-5-ylidene)-1-piperidinyl)-1-ethylsulfide hydrochloride | 429 | 0.85 | B |
| 266 | 2-(4-(5H-Dibenzo[a,d]cyclohepten-5-ylidene)-1-piperidinyl)-4-amino-6,7-dimethoxyquinazoline dihydrochloride | 476 | 0.34 | B |
| 267 | N-Acetyl-N-(3-(4-(5H-Dibenzo[a,d]cyclohepten-5-ylidene)-1-piperidinyl)-1-propyl)cyclohexylamine hydrochloride | 454 | 0.35 | B |
| 268 | N-(4-(4-(5H-Dibenzo[a,d]cyclohepten-5-ylidene)-1-piperidinyl)-1-butyl)-2-piperidone hydrochloride | 426 | 0.39 | B |
| 269 | 1-(4-(4-(5H-Dibenzo[a,d]cyclohepten-5-ylidene)-1-piperidinyl)-1-butyl)-1-ethoxycarboxylcyclohexane hydrochloride | 483 | 0.82 | B |
| 270 | 3-(4-(5H-Dibenzo[a,d]cyclohepten-5-ylidene)-1-piperidinyl)-1-(3-pyridyl)propane dihydrochloride | 392 | 0.44 | B |
| 271 | 4-(4-(5H-Dibenzo[a,d]cyclohepten-5-ylidene)-1-piperidinyl)-3',4'-dimethoxybutyrophenone N-oxide | 477(M-18) | 0.45 | B |
| 272 | 1-(4-(4-(5H-Dibenzo[a,d]cyclohepten-5-ylidene)-1-piperidinyl)-1-butyl)-1-hydroxymethylcyclohexane hydrochloride | 441 | 0.55 | B |
| 273 | 1-Acetoxymethyl-1-(4-(4-(5H-dibenzo[a,d]cyclohepten-5-ylideae)-1-piperidinyl)-1-butyl)cyclohexane hydrochloride | 483 | 0.86 | B |
| 274 | 4-(4-(5H-Dibenzo[a,d]cyclohepten-5-ylidene)-1-piperidinyl)-2-metyl-3',4'-dimethoxybutyrophenone hydrochloride | 493 | 0.22 | B |
| 275 | 4-(4-(5H-Dibenzo[a,d]cyclohepten-5-ylidene)-1-piperidinyl)-2-(2-propyl)-3',4'-dimethoxybutyrophenone hydrochloride | 521 | 0.28 | H |
| 276 | 2-Allyl-4-(4-(5H-dibenzo[a,d]cyclohepten-5-ylidene)-1-piperidinyl)-3',4'-dimethoxybutyrophenone hydrochloride | 519 | 0.30 | H |
| 277 | 4-(4-(5H-Dibenzo[a,d]cyclohepten-5-ylidene)-1-piperidinyl)-2-(1-propyl)-3',4'-dimethoxybutyrophenone hydrochloride | 521 | 0.38 | H |
| 278 | 4-(4-(5H-Dibenzo[a,d]cyclohepten-5-ylidene)-1-piperidinyl)-2-ethyl-3',4'-dimethoxybutyrophenone hydrochloride | 507 | 0.33 | H |
| 279 | Cyclohexylmethyl-2-(4-(5H-Dibeazo[a,d]cyclohepten-5-ylidene)-1-piperidinyl)-2-ethyl)ether hydrochloride | 413 | 0.73 | B |
| 280 | 1-(N-Acetyl-3-piperidinyl)-3-(4-(5H-dibenzo[a,d]cyclohepten-5-ylidene)-1-piperidinyl)propane hydrochloride | 440 | 0.75 | B |
| 281 | 3-(4-(5H-Dibenzo[a,d]cyclohepten-5-ylidene)-1-piperidinyl)-1-(3-piperidinyl)propane dihydrochloride | 398 | 0.16 | A |
| 282 | 1-(3-Acetylamino-4-methoxyphenyl)-4-(4-(5H-dibenzo[a,d]cyclohepten-5-ylidene)-1-piperidinyl)butane hydrochloride | 492 | 0.58 | B |
| 283 | 4-(4-(5H-Dibenzo[a,d]cyclohepten-5-ylidene)-1-piperidinyl)-1-butyl)cyclohexanone hydrochloride | 425 | 0.63 | B |
| 284 | 3-(4-(5H-Dibenzo[a,d]cyclohepten-5-ylidene)-1-piperidinyl)-1-(2-pyridyl)-1-propene dihydrochloride | 390 | 0.66 | H |
| 285 | 2,6-Dimethyl-4-(4-(4-(5H-dibenzo[a,d]cyclohepten-5-ylidene)-1-piperidinyl)butyl)-5-methyl-1,4- | 528 | 0.30 | F |

-continued

| exp | compound | MS(M+) | TLC (Rf) | solvent |
|---|---|---|---|---|
| | dihydropyrydine-3,5-dicarboxylate hydrochloride | | | |
| 286 | 3-(4-(5H-Dibenzo[a,d]cyclohepten-5-ylidene)-1-piperidinyl)-1-(2,3-dimethoxyphenyl)propane hydrochloride | 451 | 0.68 | H |
| 287 | 2-(4-(5H-Dibenzo[a,d]cyclohepten-5-ylidene)-1-piperidinyl)methyl-5',6'-dimethoxyindan hydrochloride | 463 | 0.59 | H |
| 288 | 2,6-Dimethyl-4-(4-(4-(5H-dibenzo[a,d]cyclohepten-5-ylidene)-1-piperidinyl)-1-butyl)-5-methylpyridine-3,5-dicarboxylate dihydrochloride | 527 | 0.68 | B |
| 289 | 3-(4-(5H-Dibenzo[a,d]cyclohepten-5-ylidene)-1-piperidinyl)-1-(4-pyridyl)propane dihydrochloride | 392 | 0.37 | B |
| 290 | N-(2-(4-(5H-Dibenzo[a,d]cyclohepten-5-ylidene)-1-piperidinyl)ethyl-3-nitrobenzamide hydrochloride | 466(H+) | 0.48 | D |
| 291 | N-(2-(5H-Dibenzo[a,d]cyclohepten-5-ylidene)-1-piperidinyl)ethyl-2-nitrobenzamide hydrochloride | 466(H+) | | D |
| 292 | N-(2-(5H-Dibenzo[a,d]cyclohepten-5-ylidene)-1-piperidinyl)ethyl-3,4-dimethoxybenzamide hydrochloride | 481(H+) | 0.31 | D |
| 293 | 4-(4-(5H-Dibenzo[a,d]cyclohepten-5-ylidene)-1-piperidinyl)-1-(2-pyrolle)-1-butanone hydrochloride | 409(H+) | | B |
| 294 | 1-(N-Acetyl-2-piperidinyl)-3-(4-(5H-dibenzo[a,d]cyclohepten-5-ylidene)-1-piperidinyl)propane hydrochloride | 440 | 0.30 | B |
| 295 | 4-(4-(5H-Dibenzo[a,d]cyclohepten-5-ylidene)-1-piperidinyl)-1-(N-methyl-3-piperidinyl)butane dihydrochloride | 426 | 0.07 | B |
| 296 | 1-(1-(4-Hydroxy)cyclohexyl)-4-(4-(5H-dibenzo[a,d]cyclohepten-5-ylidene)-1-piperidinyl)butane hydrochloride | 427 | 0.45 | B |
| 297 | 1-(1-(4-Cyano)cyclohexyl)-4-(4-(5H-dibenzo[a,d]cyclohepten-5-ylidene)-1-piperidinyl)butane hydrochloride | 436 | 0.55 | F |
| 298 | 3-(4-(5H-Dibenzo[a,d]cyclohepten-5-ylidene)-1-piperidinyl)-1-(2-methoxyphenyl)propane hydrochloride | 421 | 0.81 | B |
| 299 | 1-(1-(3-Methoxy)cyclohexyl)-4-(4-(5H-dibenzo[a,d]cyclohepten-5-ylidene)-1-piperidinyl)butane hydrochloride | 441 | 0.71 | B |
| 300 | 1-(1-(3-Hydroxyoxy)cyclohexyl)-4-(4-(5H-dibenzo[a,d]cyclohepten-5-ylidene)-1-piperidinyl)butane hydrochloride | 427 | 0.47 | B |
| 301 | 3-(4-(4-(5H-Dibenzo[a,d]cyclohepten-5-ylidene)-1-piperidinyl)-1-butyl)cyclohexanone hydrochloride | 425 | 0.70 | B |
| 302 | 4-(5H-Dibenzo[a,d]cyclohepten-5-ylidene)-1-(2-nitrocinnamyl)piperidine hydrochloride | 434 | 0.91 | B |
| 303 | 1-(2-Aminocinnamyl)-4-(4-(5H-dibenzo[a,d]cyclohepten-5-ylidene)piperidine dihydrochloride | 404 | 0.62 | B |
| 304 | 1-(2-Acetylaminamyl)-4-(5H-dibenzo[a,d]cyclohepten-5-ylidene)piperidine hydrochloride | 446 | 0.55 | B |
| 305 | 4-(4-(5H-Dibenzo[a,d]cyclohepten-5-ylidene)-1-piperidinyl)-1-butyl) tetrahydropyran hydrochloride | 413 | 0.69 | B |
| 306 | 4-(5H-Dibenzo[a,d]cyclohepten-5-ylidene)-1-(3-nitrocinnamyl)piperidine hydrochloride | 984 | 0.90 | B |
| 307 | 3-(4-(5H-Dibenzo[a,d]cyclohepten-5-ylidene)-1-piperidinyl)-1-(2-piperidinyl)propane dihydrochloride | 398 | 0.07 | B |
| 308 | 1-(N-Acetyl-4-piperidinyl)-3-(4-(5H-dibenzo[a,d]cyclohepten-5-ylidene)-1-piperidinyl)propane hydrochloride | 440 | 0.23 | B |
| 309 | 3-(4-(5H-Dibenzo[a,d]cyclohepten-5-ylidene)-1-piperidinyl)-1-(4-piperidinyl)propane dihydrochloride | 398 | 0.03 | A |
| 310 | 2-(2-(4-(5H-Dibenzo[a,d]cyclohepten-5-ylidene)-1-piperidinyl)-1-ethyl)indane hydrochloride | 417 | 0.59 | H |
| 311 | 4-(2-(4-(5H-Dibenzo[a,d]cyclohepten-5-ylidene)-1-piperidinyl)-1-ethyl)-2,4,5,6-tetramethyl-1,4-dihydropyrydine-3,5-dicarboxylate hydrochloride | 524 | 0.68 | B |
| 312 | 4-(4-(5H-Dibenzo[a,d]cyclohepten-5-ylidene)-1-piperidinyl)-1-(N-ethoxycarbonyl-3-piperidinyl)butane hydrochloride | 484 | 0.64 | B |
| 313 | 1-(5-(4-(5H-Dibenzo[a,d]cyclohepten-5-ylidene)-1-piperidinyl)-1-pentyl)-1-methoxycarbonylcyclohexane hydrochloride | 483 | 0.72 | B |
| 314 | 1-(3-(4-(5H-Dibenzo[a,d]cyclohepten-5-ylidene)-1-piperidinyl)-1-propyl)-1-methoxycarbonylcyclohexane hydrochloride | 455 | 0.75 | B |
| 315 | 1-(3-Aminophenyl)-3-(4-(5H-dibenzo[a,d]cyclohepten-5-ylidene)-1-piperidinyl)propane dihydrochloride | 993 | 0.62 | B |
| 316 | 1-(3-Acetylaminophenyl)-3-(4-(5H-dibenzo[a,d]cyclohepten-5-ylidene)-1-piperidinyl)propane hydrochloride | 994 | 0.48 | B |
| 317 | 3-(4-(5H-Dibenzo[a,d]cyclohepten-5-ylidene)-1-piperid 0.4inyl)-1-(3,4,5-trimetoxyphenyl)propane dihydrochloride | 481 | 0.65 | B |
| 318 | 2-(3-(4-(5H-Dibenzo[a,d]cyclohepten-5-ylidene)-1-piperidinyl)-1-ethyl)-5,6-dimethoxy-1,2,3,4-tetrahydronaphtalene hydrochloride | 491 | 0.21 | H |
| 319 | 6-(4-(5H-Dibenzo[a,d]cyclohepten-5-ylidene)-1-piperidinyl)methyl-2,3-dimethoxybenzocycloheptene hydrochloride | 491 | 0.56 | H |
| 320 | 4-(5H-Dibenzo[a,d]cyclohepten-5-ylidene)-1-(3,4,5-trimethoxycinnamyl)piperidine hydrochloride | 479 | 0.69 | B |
| 321 | 1-(N-Acetyl-4-piperidinyl)-5-(4-(5H-dibenzo[a,d]cyclohepten-5-ylidene)-1-piperidinyl)-1-pentene dihydrochloride | 466 | 0.33 | B |
| 322 | 2-(4-(4-(5H-Dibenzo[a,d]cyclohepten-5-ylidene)-1-piperidinyl)-1-butyl)-3,4,5,6-tetramethyl-1,4-dihydropyrydine-3,5-dicarboxylate hydrochloride | 1000 | 0.30 | B |
| 323 | 2-(4-(4-(5H-Dibenzo[a,d]cyclohepten-5-ylidene)-1-piperidinyl)-1-butyl)-3,4,5,6-tetramethylpyridine-3,5-dicarboxylate hydrochloride | 550 | 0.43 | B |
| 324 | 1-(1-(4-Methoxy)cyclohexyl)-3-(4-(5H-dibenzo[a,d]cyclohepten-5-ylidene)-1-piperidinyl)propane hydrochloride | 427 | 0.48 | B |
| 325 | 4-(5H-Dibenzo[b,e]thiepin-5-ylidene)-1-(4-nitrocinnamyl)piperidine hydrochloride | 454 | 0.89 | B |
| 326 | 1-(4-Aminocinnamyl)-4-(5H-dibeazo[b,e]thiepin-5-ylideae)piperidine dihydrochloride | 424 | 0.65 | B |
| 327 | 1-(4-Acetylaminominocinnamyl)-4-(5H-Dibenzo[b,e]thiepin-5-ylideae)piperidine hydrochloride | 466 | 0.58 | B |
| 328 | 3-(4-(5H-Dibenzo[a,d]cycloheptea-5-ylidene)-1-piperidinyl)-1-(2,4-dimetoxyphenyl)propane dihydrochloride | 451 | 0.64 | B |
| 329 | 2-(4-(5H-Dibenzo[a,d]cycloheptea-5-ylidene)-1-piperidinyl)methyl-4'-nitroindan hydrochloride | 448 | 0.49 | I |
| 330 | 4'-Amino-2-(4-(5H-Dibenzo[a,d]cyclohepten-5-ylidene)-1-piperidinyl)methylindan hydrochloride | 418 | 0.38 | H |
| 331 | 4'-Acetylamino-2-(4-(5H-Dibenzo[a,d]cyclohepten-5-ylidene)-1-piperidinyl)methylindan hydrochloride | 460 | 0.33 | B |
| 332 | 2-(4-(5H-Dibenzo[a,d]cyclohepten-5-ylidene)-1-piperidinyl)methyl-5-'-nitroindan hydrochloride | 448 | 0.50 | I |
| 333 | 5'-Amino2-(4-(5H-Dibenzo[a,d]cyclohepten-5-ylidene)-1-piperidinyl)methylindan hydrochloride | 418 | 0.34 | B |
| 334 | 5'-Acetylamino-2-(4-(5H-Dibenzo[a,d]cyclohepten-5-ylidene)-1-piperdinyl)methylindane hydrochloride | 460 | 0.29 | H |
| 335 | 4-Amino-N-(2-(5H-Dibenzo[a,d]cyclohepten-5-ylidene)-1-piperidinyl)ethylbenzamide hydrochloride | 435 | | B |
| 336 | 3-Amino-N-(2-(5H-Dibenzo[a,d]cyclohepten-5-ylidene)-1-piperidinyl)ethylbenzamide hydrochloride | 435 | | B |
| 337 | 1-Formyl-N-(2-(5H-dibenzo[a,d]cyclohepten-5-ylidene)-1-piperidinyl)ethyisonipecotinamide hydrochloride | 455 | | B |
| 338 | 1-Formyl-N-(2-(5H-dibenzo[a,d]cyclohepten-5-ylidene)-1-piperidinyl)ethynipecotinamide hydrochloride | 455 | | B |

-continued

| exp | compound | MS(M+) | TLC (Rf) | solvent |
|---|---|---|---|---|
| 339 | N-(2-(5H-Dibenzo[a,d]cyclohepten-5-ylidene)-1-piperidinyl)ethynicotinamide dihydrochloride | 421 | 0.42 | B |
| 340 | N-(2-(5H-Dibenzo[a,d]cyclohepten-5-ylidene)-1-piperidinyl)ethynicotinamide N-oxide hydrochloride | 437(H+) | 0.27 | D |
| 341 | N-(2-(5H-Dibenzo[a,d]cyclohepten-5-ylidene)-1-piperidinyl)ethyisonicotinamide N-oxide hydrochloride | 437(H+) | 0.30 | D |
| 342 | 4-(5H-Dibenzo[a,d]cyclohepten-5-ylidene)-1-(2,4-dimethoxycinnamyl)piperidine hydrochloride | 449 | 0.73 | B |
| 343 | 4-(5H-Dibenzo[a,d]cyclohepten-5-ylidene)-1-(2,5-dimethoxycinnamyl)piperidine hydrochloride | 449 | 0.73 | B |
| 344 | 4-(5H-Dibenzo[a,d]cyclohepten-5-ylidene)-1-(2,3-dimethoxycinnamyl)piperidine hydrochloride | 449 | 0.90 | B |
| 345 | 4-(5H-Dibenzo[a,d]cyclohepten-5-ylidene)-1-(3,5-dimethoxycinnamyl)piperidine hydrochloride | 449 | 0.74 | B |
| 346 | 1-(4-Cyanocinnamyl)-4-(5H-dibenzo[a,d]cyclohepten-5-ylidene)piperidine hydrochloride | 414 | 0.70 | B |
| 347 | 4-(5H-Dibenzo[a,d]cyclohepten-5-ylidene)-1-(2-methoxycinnamyl)piperidine hydrochloride | 419 | 0.87 | B |
| 348 | 4-(5H-Dibenzo[a,d]cyclohepten-5-ylidene)-1-(3-methoxycinnamyl)piperidine hydrochloride | 419 | 0.89 | B |
| 349 | 4-(5H-Dibenzo[a,d]cyclohepten-5-ylidene)-1-(4-methoxycinnamyl)piperidine hydrochloride | 419 | 0.85 | B |
| 350 | 4-(10.11-Dihydro-5H-dibenzo[a,d]cyclohepten-5-ylidene)-1-(4-nitrocinnamyl)piperidine hydrochloride | 436 | 0.93 | B |
| 351 | 1-(4-Aminocinnamyl)-4-(10.11-dihydro-5H-dibenzo[a,d]cyclohepten-5-ylidene)piperidine dihydrochloride | 406 | 0.64 | B |
| 352 | 1-(4-Acetylaminocinnamyl)-4-(10.11-dihydro5H-dibenzo[a,d]cyclohepten-5-ylidene)piperidine dihydrochloride | 448 | 0.54 | B |
| 353 | 4-(5H-Dibenzo[a,d]cyclohepten-5-ylidene)-1-(4-fluorocinnamyl)piperidine hydrochloride | 407 | 0.88 | B |
| 354 | 2-(2-(4-(5H-Dibenzo[a,d]cyclohepten-5-ylidene)-1-piperidinyl)-1-ethyl)-4'-nitroindan hydrochloride | 462 | 0.34 | H |
| 355 | 4'-Amino-2-(2-(4-(5H-Dibenzo[a,d]cyclohepten-5-ylidene)-1-piperidinyl)-1-ethyl)indan hydrochloride | 432 | 0.53 | B |
| 356 | 4'-Acetylamino-2-(2-(4-(5H-Dibenzo[a,d]cyclohepten-5-ylidene)-1-piperidinyl)-1-ethyl)indan hydrochloride | 474 | 0.24 | B |
| 357 | 2-(2-(4-(5H-Dibenzo[a,d]cyclohepten-5-ylidene)-1-piperidinyl)-1-ethyl)-5'-nitroindan hydrochloride | 462 | 0.31 | H |
| 358 | 5'-Amino-2-(2-(4-(5H-Dibenzo[a,d]cyclohepten-5-ylidene)-1-piperidinyl)-1-ethyl)indan dihydrochloride | 432 | 0.23 | H |
| 359 | 5'-Acetylamino-2-(2-(4-(5H-Dibenzo[a,d]cyclohepten-5-ylidene)-1-piperidinyl)-1-ethyl)indan hydrochloride | 474 | 0.05 | H |
| 360 | 2-(2-(4-(5H-Dibenzo[a,d]cyclohepten-5-ylidene)-1-piperidinyl)-1-ethyl)-5'-methanesulfonylaminoindan hydrochloride | 510 | 0.11 | H |
| 361 | 1-Cyclohexyl-4-(4-(10.11-dihydroxy-5H-dibenzo[a,d]cyclohepten-5-ylidene)-1-piperidinyl)butane | 445 | 0.84 | B |
| 362 | 3-(4-(5H-Dibenzo[a,d]cyclohepten-5-ylidene)-1-piperidinyl)-1-(3-pyridyl)-1-propene dihydrochloride | 390 | 0.44 | B |
| 363 | 4-(5H-Dibenzo[a,d]cyclohepten-5-ylidene)-1-(4-hydroxycinnamyl)piperidine hydrochloride | 406(H+) | 0.55 | B |
| 364 | 1-(4-Acetoxycinnamyl)-4-(5H-dibenzo[a,d]cyclohepten-5-ylidene)piperidine hydrochloride | 447 | 0.87 | B |
| 365 | 4-(5H-Dibenzo[a,d]cyclohepten-5-ylidene)-1-(4-hydroxy-3-methoxycinnamyl)piperidine hydrochloride | 435 | 0.63 | B |
| 366 | 1-(4-Acetoxy-3-metoxycinnamyl)-4-(5H-dibenzo[a,d]cyclohepten-5-ylidene)piperidine hydrochloride | 477 | 0.83 | B |
| 367 | 4-(5H-Dibenzo[a,d]cyclohepten-5-ylidene)-1-(3-hydroxycinnamyl)piperidine hydrochloride | 405 | 0.45 | B |
| 368 | 1-(3-Acetoxycinnamyl)-4-(5H-dibenzo[a,d]cyclohepten-5-ylidene)piperidine hydrochloride | 447 | 0.80 | B |
| 369 | 4-(5H-Dibenzo[a,d]cyclohepten-5-ylidene)-1-(3-(2-methoxyacetoxy)cinnamyl)piperidine hydrochloride | 477 | 0.65 | B |
| 370 | 4-(5H-Dibenzo[a,d]cyclohepten-5-ylidene)-1-(4-propanoylaminocinnamyl)piperidine hydrochloride | 460 | 0.21 | H |
| 371 | 4-(5H-Dibenzo[a,d]cyclohepten-5-ylidene)-1-(4-ethoxycarbomylaminocinnamyl)piperidine hydrochloride | 476 | 0.20 | H |
| 372 | 4-(5H-Dibenzo[a,d]cyclohepten-5-ylidene)-1-(4-methanesulfonylaminocinnamyl)piperidine hydrochloride | 482 | 0.44 | B |
| 373 | 1-(N,N,-Bis(methanesulfonyl)aminocinnamyl)-4-(5H-Dibenzo[a,d]cyclohepten-5-ylidene)piperidine hydrochloride | 560 | 0.88 | B |
| 374 | 4-(5H-Dibenzo[a,d]cyclohepten-5-ylidene)-1-(2-methoxycarbonylcinnamyl)piperidine hydrochloride | 447 | 0.55 | B |
| 375 | 4-(5H-Dibenzo[a,d]cyclohepten-5-ylidene)-1-(3-methoxycarbonylcinnamyl)piperidine hydrochloride | 447 | 0.48 | H |
| 376 | 4-(5H-Dibenzo[a,d]cyclohepten-5-ylidene)-1-(4-methoxycarbonylcinnamyl)piperidine hydrochloride | 447 | 0.50 | B |
| 377 | 4-(5H-Dibenzo[a,d]cyclohepten-5-ylidene)-1-(3-methoxy-2-nitrocinnamyl)piperidine hydrochloride | 464 | 0.30 | H |
| 378 | 4-(5H-Dibenzo[a,d]cyclohepten-5-ylidene)-1-(4-methoxycarbonylaminocinnamyl)piperidine hydrochloride | 462 | 0.53 | B |
| 379 | 4-(5H-Dibenzo[a,d]cyclohepten-5-ylidene)-1-(4-pivaloylaminocinnamyl)piperidine hydrochloride | 488 | 0.51 | B |
| 380 | 4-(5H-Dibenzo[a,d]cyclohepten-5-ylidene)-1-(4-trifluoroacetylaminocinnamyl)piperidine hydrochloride | 500 | 0.44 | B |
| 381 | 1-(4-Butanoylaminocinnamyl)-4-(5H-dibenzo[a,d]cyclohepten-5-ylidene)piperidine hydrochloride | 474 | 0.50 | B |
| 382 | 4-(5H-Dibenzo[a,d]cyclohepten-5-ylidene)-1-(4-ethoxycarboxycinnamyl)piperidine hydrochloride | 477 | 0.85 | B |
| 383 | 4-(5H-Dibenzo[a,d]cyclohepten-5-ylidene)-1-(4-(2-methoxyacetoxy)cinnamyl)piperidine hydrochloride | 477 | 0.45 | B |
| 384 | 4-(5H-Dibenzo[a,d]cyclohepten-5-ylidene)-1-(3,4-dihydroxycinnamyl)piperidine hydrochloride | 422(H+) | 0.35 | B |
| 385 | 4-(5H-Dibenzo[a,d]cyclohepten-5-ylidene)-1-(2-indolylmethyl)piperidine hydrochloride | 402 | 0.67 | H |
| 386 | 1-(4-Aminosulfonylcinnamyl)-4-(5H-dibenzo[a,d]cyclohepten-5-ylidene)piperidine hydrochloride | 468(H+) | 0.48 | B |
| 387 | 4-(5H-Dibenzo[a,d]cyclohepten-5-ylidene)-1-(3-methoxy-4-nitrocinnamyl)piperidine hydrochloride | 464 | 0.29 | H | solvent: solvent for TLC
A: chloroform/methanol = 4/1
B: chloroform/methanol = 9/1
C: chloroform/methanol = 20/1
D: chloroform/methanol = 25/1
E: chloroform/methanol = 50/1
F: ethylacetate/hexane = 5/1
G: ethylacetate/hexane = 3/1
H: ethylacetate/hexane = 1/1
I: ethylacetate/hexane = 1/2
G: ethylacetate/hexane = 1/5

EXAMPLE 154

As test animals, four male spontaneously hypertensive rats (weight 400 to 440 g) that were sufficiently adapted for feeding and in which hypertension was confirmed were used.

Physiological saline aqueous solution containing 2.5% Nicolle and 2.5% ethanol of sample was intravenously administered by bolus injection at a does of 1 ml per 1 kg of body weight. Systolic blood pressure after administration was measured by the indirect (tail-cuff) method.

The results are shown below.

| Compound | Dose (mg/kg) | Decrease in systolic blood pressure (mmHg) time after administration (hour) | |
|---|---|---|---|
| | | 0.5 | 4 |
| 1 | 10 | −67 | 1 |
| 2 | 10 | −125 | −34 |
| 3 | 3 | −110 | −22 |
| 4 | 10 | −76 | 0 |
| 5 | 10 | −56 | −20 |
| 7 | 10 | −57 | −15 |
| 8 | 10 | −95 | −21 |
| 9 | 10 | −91 | −19 |
| 10 | 10 | −129 | −21 |
| 11 | 10 | −166 | |
| 12 | 10 | −27 | 1 |
| 13 | 10 | −47 | 4 |
| 14 | 10 | −105 | −10 |
| 15 | 10 | −130 | −136 |
| 16 | 10 | −114 | −30 |
| 17 | 10 | −84 | −16 |
| 20 | 10 | −37 | 2 |
| 23 | 10 | −34 | 10 |
| 25 | 10 | −8 | −7 |
| 28 | 10 | −52 | 4 |
| 31 | 10 | −61 | −11 |
| 37 | 10 | −78 | −36 |
| 38 | 10 | −140 | −76 |
| 42 | 10 | −66 | −14 |
| 45 | 10 | −147 | −38 |
| 52 | 10 | −23 | −9 |
| 59 | 10 | −87 | −21 |
| 60 | 10 | −121 | −48 |
| 100 | 10 | −35 | −5 |
| 101 | 10 | −89 | −14 |
| 107 | 10 | −88 | −19 |
| 108 | 10 | −126 | −50 |
| 111 | 10 | −98 | −13 |
| 112 | 10 | −16 | 0 |
| 113 | 1 | −151 | −81 |
| 115 | 10 | −53 | −19 |
| 116 | 10 | −36 | −12 |
| 117 | 10 | −143 | −25 |
| 118 | 10 | −129 | −24 |
| 119 | 10 | −34 | −5 |
| 120 | 3 | −17 | −12 |
| 121 | 10 | −42 | −19 |
| 122 | 10 | −120 | −62 |
| 123 | 10 | −55 | −7 |
| 124 | 10 | −90 | −20 |
| 125 | 10 | −93 | −14 |
| 126 | 10 | −87 | −19 |
| 128 | 10 | −128 | −8 |
| 129 | 10 | −17 | −1 |
| 130 | 10 | −42 | −9 |
| 131 | 10 | −116 | 2 |
| 132 | 10 | −106 | −5 |
| 133 | 3 | −146 | −84 |
| 134 | 10 | −115 | −30 |
| 135 | 10 | −132 | −50 |
| 136 | 10 | −100 | −40 |
| 138 | 10 | −129 | −33 |
| 139 | 10 | −139 | −89 |
| 140 | 3 | −113 | −101 |
| 142 | 10 | −43 | 0 |
| 149 | 10 | −116 | −32 |
| 150 | 10 | −110 | −47 |
| 151 | 10 | −81 | −43 |
| 154 | 10 | −131 | −105 |
| 155 | 10 | −131 | −105 |
| 156 | 10 | −110 | −42 |
| 157 | 10 | −32 | −13 |
| 158 | 10 | −8 | 7 |
| 159 | 10 | −27 | −12 |
| 160 | 10 | −3 | −10 |
| 161 | 10 | −64 | −12 |
| 162 | 10 | −62 | −3 |
| 163 | 10 | −1 | 4 |
| 164 | 10 | −91 | −22 |
| 165 | 10 | −22 | 12 |
| 166 | 10 | −45 | 6 |
| 168 | 10 | −108 | 0 |
| 169 | 10 | −130 | −4 |
| 171 | 10 | −122 | −8 |
| 172 | 10 | −115 | −25 |
| 173 | 10 | −98 | −25 |
| 174 | 10 | −8 | −16 |
| 175 | 10 | −87 | −1 |
| 176 | 10 | −105 | −10 |
| 180 | 10 | −25 | −24 |
| 181 | 10 | −56 | −27 |
| 182 | 10 | −11 | −6 |
| 184 | 10 | −16 | −4 |
| 185 | 10 | −66 | −10 |
| 186 | 10 | −95 | −12 |
| 187 | 10 | −47 | −9 |
| 188 | 10 | −94 | −12 |
| 189 | 10 | −72 | −15 |
| 190 | 10 | −11 | −15 |
| 191 | 10 | −29 | −20 |
| 192 | 10 | −25 | −36 |
| 193 | 10 | −124 | −59 |
| 194 | 10 | −59 | −17 |
| 195 | 10 | −100 | −51 |
| 196 | 10 | −145 | −81 |
| 197 | 10 | −51 | −26 |
| 198 | 10 | −124 | −25 |
| 199 | 10 | −15 | −24 |
| 200 | 10 | −10 | −24 |
| 201 | 10 | −118 | −21 |
| 202 | 10 | −54 | −16 |
| 203 | 3 | −123 | −58 |
| 204 | 10 | −141 | −84 |
| 205 | 10 | −22 | −4 |
| 206 | 10 | −61 | −27 |
| 207 | 10 | −98 | −43 |
| 208 | 10 | −131 | −19 |
| 209 | 10 | −49 | −13 |
| 210 | 1 | −78 | −69 |
| 212 | 10 | −155 | |
| 213 | 10 | −82 | 3 |
| 214 | 10 | −126 | −21 |
| 215 | 10 | −128 | −14 |
| 216 | 3 | −2 | −27 |
| 217 | 10 | −18 | −20 |
| 218 | 10 | −97 | −11 |
| 219 | 10 | −104 | −33 |
| 220 | 10 | −148 | −54 |
| 221 | 10 | −70 | −13 |
| 222 | 10 | −94 | −5 |
| 224 | 10 | −69 | −61 |
| 225 | 10 | −115 | −31 |
| 226 | 10 | −131 | −16 |
| 228 | 3 | −112 | −14 |
| 229 | 3 | −77 | −14 |
| 230 | 3 | −131 | −91 |
| 231 | 3 | −132 | −115 |
| 232 | 1 | −92 | −85 |
| 233 | 10 | −35 | −1 |
| 234 | 10 | −96 | −2 |
| 235 | 10 | −99 | −5 |
| 236 | 10 | −10 | −15 |
| 237 | 10 | −65 | −14 |
| 238 | 10 | −14 | −5 |
| 239 | 10 | −68 | −15 |
| 240 | 3 | −118 | −5 |
| 241 | 10 | −73 | −4 |
| 242 | 10 | −28 | 7 |
| 243 | 10 | −111 | −31 |
| 244 | 10 | −19 | 4 |
| 245 | 10 | −34 | −10 |
| 246 | 10 | −34 | −4 |
| 247 | 10 | −119 | −40 |
| 248 | 10 | −101 | −92 |
| 249 | 10 | −121 | −100 |
| 250 | 10 | −136 | −30 |
| 251 | 10 | −110 | −24 |
| 252 | 10 | −23 | −5 |
| 253 | 10 | −12 | 1 |
| 255 | 10 | −62 | 2 |
| 256 | 10 | −60 | −11 |

| Compound | Dose (mg/kg) | Decrease in systolic blood pressure (mmHg) time after administration (hour) 0.5 | 4 |
|---|---|---|---|
| 257 | 10 | −70 | −13 |
| 258 | 10 | −74 | −10 |
| 259 | 10 | −46 | −5 |
| 260 | 10 | −51 | −10 |
| 261 | 10 | −123 | −11 |
| 262 | 10 | −16 | −3 |
| 264 | 10 | −38 | −5 |
| 265 | 10 | −61 | −11 |
| 266 | 10 | −133 | −77 |
| 267 | 10 | −40 | 0 |
| 268 | 10 | −29 | 13 |
| 269 | 10 | −143 | −71 |
| 270 | 10 | −18 | 2 |
| 271 | 10 | −17 | −13 |
| 272 | 10 | −76 | −3 |
| 273 | 10 | −37 | 5 |
| 274 | 10 | −102 | −21 |
| 275 | 10 | −66 | −20 |
| 276 | 10 | −24 | −1 |
| 277 | 10 | −27 | 0 |
| 278 | 10 | −64 | 2 |
| 279 | 3 | −83 | −24 |
| 280 | 10 | −50 | −11 |
| 281 | 10 | −31 | −5 |
| 282 | 10 | −72 | −15 |
| 283 | 10 | −112 | 4 |
| 284 | 3 | −151 | −40 |
| 285 | 10 | −62 | −7 |
| 286 | 10 | −134 | −40 |
| 287 | 10 | −83 | −16 |
| 288 | 10 | −92 | −14 |
| 289 | 3 | −20 | 10 |
| 290 | 3 | −15 | 15 |
| 291 | 3 | −8 | 15 |
| 292 | 3 | −31 | 3 |
| 293 | 10 | −122 | 4 |
| 294 | 3 | −17 | 7 |
| 295 | 3 | −36 | 1 |
| 296 | 10 | −109 | −14 |
| 297 | 10 | −129 | −57 |
| 298 | 10 | −111 | −31 |
| 299 | 10 | −134 | −45 |
| 300 | 10 | −97 | −22 |
| 301 | 10 | −100 | −12 |
| 302 | 10 | −83 | −41 |
| 303 | 3 | −90 | −19 |
| 304 | 10 | −49 | −5 |
| 305 | 10 | −95 | −9 |
| 306 | 10 | −138 | −37 |
| 307 | 10 | −62 | −10 |
| 308 | 3 | −27 | −5 |
| 310 | 10 | −90 | −18 |
| 311 | 10 | −90 | −18 |
| 312 | 10 | −115 | −11 |
| 313 | 10 | −154 | −85 |
| 314 | 10 | −61 | −11 |
| 315 | 10 | −43 | −3 |
| 316 | 1 | −100 | 8 |
| 317 | 10 | −118 | −14 |
| 318 | 10 | −83 | −57 |
| 319 | 10 | −104 | −20 |
| 320 | 10 | −147 | −113 |
| 321 | 10 | −60 | −4 |
| 322 | 10 | −100 | −16 |
| 323 | 10 | −117 | −11 |
| 324 | 10 | −137 | −46 |
| 325 | 10 | −115 | −100 |
| 326 | 1 | −125 | −102 |
| 327 | 3 | −10 | −43 |
| 328 | 10 | −125 | −87 |
| 329 | 10 | −34 | −7 |
| 330 | 10 | −93 | −25 |
| 331 | 10 | −62 | −14 |
| 332 | 10 | −111 | −57 |
| 343 | 3 | −83 | −45 |
| 344 | 1 | −123 | −35 |
| 345 | 3 | −120 | −95 |
| 346 | 3 | −142 | −121 |
| 347 | 3 | −116 | −53 |
| 348 | 3 | −105 | −12 |
| 349 | 1 | −48 | −43 |
| 350 | 10 | −136 | −85 |
| 351 | 3 | −70 | −21 |
| 352 | 3 | −93 | −60 |
| 353 | 10 | −147 | −138 |
| 354 | 3 | −89 | −8 |
| 363 | 3 | −120 | |
| 364 | 1 | −113 | |
| 365 | 3 | −80 | −56 |
| 366 | 3 | −152 | −113 |
| 367 | 10 | −98 | −63 |
| 368 | 3 | −110 | −68 |
| 369 | 10 | −101 | −83 |
| 370 | 10 | −99 | −69 |
| 374 | 3 | −119 | 11 |
| 375 | 1 | −126 | −70 |
| 376 | 3 | −106 | −77 |
| 377 | 1 | −151 | −73 |
| 378 | 1 | −106 | −90 |
| 379 | 1 | −118 | −59 |
| 380 | 0.3 | −141 | |
| 381 | 3 | −136 | |
| 382 | 3 | −129 | −74 |
| 383 | 3 | −112 | −86 |
| 384 | 3 | −130 | −93 |
| 385 | 10 | −123 | −96 |
| 386 | 10 | −83 | −96 |
| 387 | 10 | −112 | −50 |

Effects of the Invention

From the foregoing results, it is understood that the piperidine derivatives of the present invention possess hypotensive activity and are usable as hypotensives and therefore, they can be expected to provide an excellent hypotensive effect. Accordingly, the present invention is extremely useful, particularly in the pharmaceutical industry.

Having now fully described the invention, it will be apparent to one of ordinary skill in the art that many changes and modifications can be made thereto without departing from the spirit or scope of the invention as set forth herein.

What is claimed as new and is intended to be secured by Letters Patent of the United States is:

1. A piperidine compound of the formula (I)

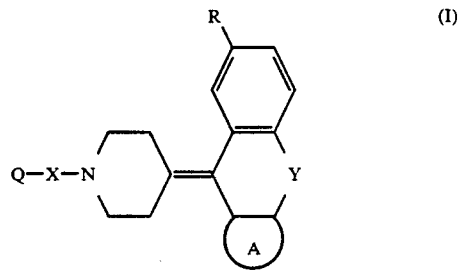

having antihypertensive activity in mammals, wherein:
A is thiophene or pyridine;
R is —H, Cl or —OCH$_3$;
X is —CH=CH—CH$_2$— or substituted or unsubstituted $+CH_2\!\!\!\!+_n$ in which n is an integer of from 0 to 10;
Y is —CH=CH—, —CH₂CH₂—, —CH₂CO—, —O—, —S—, —NH—, —OCH₂—, —SCH₂—, —NHCH₂—, —CH(OH)CH₂— or —CH(OH)CH(OH)—;
Q is substituted or unsubstituted in n-hexyl, substituted or unsubstituted carboxypropyl, substituted or unsubstituted ethoxycarbonylpropyl, substituted or unsubstituted cyanopropyl, substituted or unsubstituted cyclohexyl, substituted or unsubstituted indanyl, substituted or unsubstituted naphthyl, substituted or unsubstituted tetrahydronaphthyl, substituted or unsubstituted benzocycloheptyl, substituted or unsubstituted piperidinyl, substituted or unsubstituted tetrahydroisoquinolinyl, substituted or unsubstituted indolyl, substituted or unsubstituted pyrolyl, substituted or unsubstituted furyl, substituted or unsubstituted thienyl, substituted or unsubstituted thiazolyl or substituted or unsubstituted oxazolyl;
wherein any one or more of the $+CH_2+$ groups of the hexyl, carboxypropyl, ethoxycarbonylpropyl and cyanopropyl may be replaced by —CH=CH, —C≡C—, —O—, —S—, —NH—, —N(COCH₃—, —N(COC₂H₅)—, —N(CHO)—, —N(CH₃—, —CO—, —SO— or —SO₂—;
wherein the hydrogen atoms of one or more of the $+CH_2+$ groups in X and Q may be substituted by $+CH_2\!\!\!\!+_4$ or $+CH_2\!\!\!\!+_5$ thereby forming a ring structure;
wherein the substituted members of the groups X and Q are substituted by at least one substituent selected from the group consisting of H$+CH_2\!\!\!\!+_n$ wherein n is an integer of 1 to 10, Cl$+CH_2\!\!\!\!+_3$ allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

2. A piperdine compound of the formula (I)

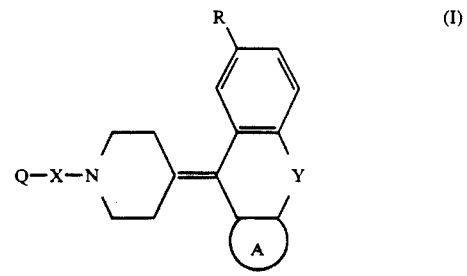

having antihypertensive activity in mammals, wherein:
A is benzene;
R is —H, Cl or —OCH₃;
X is —CH=CH—CH₂— or substituted or unsubstituted $+CH_2\!\!\!\!+_n$ in which n is an integer of from 0 to 10;
Y is —CH₂CH₂—, —SCH₂—;
Q is substituted or unsubstituted in n-hexyl, substituted or unsubstituted carboxypropyl, substituted or unsubstituted ethoxycarbonylpropyl, substituted or unsubstituted cyanopropyl, substituted or unsubstituted cyclohexyl, substituted or unsubstituted indanyl, substituted or unsubstituted naphthyl, substituted or unsubstituted tetrahydronaphthyl, substituted or unsubstituted benzocycloheptyl, substituted or unsubstituted piperidinyl, substituted or unsubstituted tetrahydroisoquinolinyl, substituted or unsubstituted indolyl, substituted or unsubstituted pyrolyl, substituted or unsubstituted furyl, substituted or unsubstituted thienyl, substituted or unsubstituted thiazolyl or substituted or unsubstituted oxazolyl;
wherein any one or more of the $+CH_2+$ groups of the hexyl, carboxypropyl, ethoxycarbonylpropyl and cyanopropyl may be replaced by —CH=CH, —C≡C—, —O—, —S—, —NH—, —N(COCH₃—, —N(COC₂H₅)—, —N(CHO)—, —N(CH₃—, —CO—, —SO— or —SO₂—;
wherein the hydrogen atoms of one or more of the $+CH_2+$ groups in X and Q may be substituted by $+CH_2\!\!\!\!+_4$ or $+CH_2\!\!\!\!+_5$ thereby forming a ring structure;
wherein the substituted members of the groups X and Q are substituted by at least one substituent selected from the group consisting of H$+CH_2\!\!\!\!+_n$ wherein n is an integer of 1 to 10,

allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

3. A piperidine compound of the formula (I)

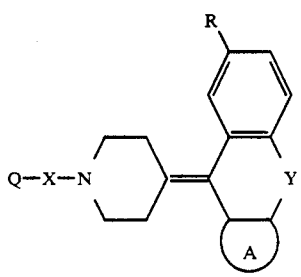

(I)

having antihypertensive activity in mammals, wherein:
A is benzene;
R is —H, Cl or —OCH$_3$;
X is —CH=CH—CH$_2$—;
Y is —CH=CH—, —CH$_2$CH$_2$— or —SCH$_2$—;
Q is phenyl substituted by at least one substituent selected from the group consisting of

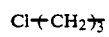

allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

4. The piperdine compound of claim 1, wherein X and Q are substituted by at least one substituent selected from the group consisting of H(CH$_2$)$_n$, wherein n is 1 to 10, Cl(CH$_2$)$_3$, allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

5. The piperdine compound of claim 1, wherein A is pyridine.

6. The piperdine compound of claim 1, wherein A is thiophene.

7. The piperdine compound of claim 2, wherein Q is substituted or unsubstituted indanyl, substituted or unsubstituted naphthyl, substituted or unsubstituted tetrahydronaphthyl, substituted or unsubstituted benzocycloheptyl, substituted or unsubstituted piperidinyl, substituted or unsubstituted tetrahydroisoquinolinyl, substituted or unsubstituted indolyl, substituted or unsubstituted pyrolyl, substituted or unsubstituted furyl, substituted or unsubstituted thienyl, substituted or unsubstituted thiazolyl or substituted or unsubstituted oxazolyl; and wherein the substituted members of the groups X and Q are substituted by at least one substituent selected from the groups consisting of hydroxy, methoxy, ethoxy, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

8. The piperdine compound of claim 5, which is 1-(4-aminosulfonylcinnamyl)-4-(5H-dibenzo [a,d]cyclohepten-5-ylidene)piperidine.

9. The piperdine compound of claim 3, wherein R is —H, X is —CH=CH—CH$_2$—; Y is —CH=CH—, —CH$_2$CH$_2$— or —SCH$_2$—; and Q is aminosulfonylphenyl.

* * * * *